United States Patent [19]
de Boer

[11] Patent Number: 5,874,082
[45] Date of Patent: Feb. 23, 1999

[54] HUMANIZED ANTI-CD40 MONOCLONAL ANTIBODIES AND FRAGMENTS CAPABLE OF BLOCKING B CELL PROLIFERATION

[75] Inventor: Mark de Boer, Heemskerk, Netherlands

[73] Assignee: Chiron Corporation, Emeryville, Calif.

[*] Notice: The term of this patent shall not extend beyond the expiration date of Pat. Nos. 5,667,165 and 5,677,165.

[21] Appl. No.: 606,293

[22] Filed: Feb. 23, 1996

Related U.S. Application Data

[63] Continuation-in-part of Ser. No. 70,158, May 28, 1993, Pat. No. 5,677,165, which is a continuation-in-part of Ser. No. 910,222, Jul. 9, 1992, Pat. No. 5,397,703.

[51] Int. Cl.$^6$ .......................... A61K 39/395; C07K 16/28
[52] U.S. Cl. ..................................... 424/153.1; 424/130.1; 424/133.1; 424/141.1; 424/143.1; 424/144.1; 424/153.1; 424/173.1; 530/387.3; 530/388.22; 530/388.7; 530/388.73
[58] Field of Search .............................. 424/120.1, 133.1, 424/141.1, 144.1, 152.1, 153.1, 154.1, 172.1, 173.1; 530/387.1, 387.3, 388.1, 388.22, 388.7, 388.73

[56] References Cited

U.S. PATENT DOCUMENTS

| | | |
|---|---|---|
| 4,355,023 | 10/1982 | Ehrlich et al. . |
| 4,689,299 | 8/1987 | Insel et al. . |
| 4,886,796 | 12/1989 | Eichner et al. . |
| 4,923,872 | 5/1990 | Kostlan et al. . |
| 5,068,223 | 11/1991 | Lipsky et al. . |
| 5,100,899 | 3/1992 | Calne . |
| 5,182,368 | 1/1993 | Ledbetter et al. . |
| 5,677,165 | 10/1997 | De Boer et al. . |

FOREIGN PATENT DOCUMENTS

| | | |
|---|---|---|
| 0 434 879 A1 | 7/1991 | European Pat. Off. . |
| 0 555 880 A2 | 8/1993 | European Pat. Off. . |
| WO 90/07861 | 7/1990 | WIPO . |
| WO 94/04570 | 3/1992 | WIPO . |
| 9308207 | 4/1993 | WIPO . |
| WO 93/11794 | 6/1993 | WIPO . |
| WO 94/01547 | 1/1994 | WIPO . |
| WO 95/09653 | 4/1995 | WIPO . |

OTHER PUBLICATIONS

Winter et al., "Antibody–based Therapy, Humanized Antibodies," *TIPS*, 14:139–143 (1993).
Gray et al., "Memory B Cell Development But Not Germinal Center Formation Is Impaired By In Vivo Blockade Of CD40–CD40 Ligand Interaction," *J. Exp. Med.*, 180:141–155 (Jul. 1994).
Stuber et al., "Blocking the CD40L–CD40 Interaction In Vivo Specifically Prevents The Priming Of T Helper 1 Cells Through The Inhibition Of Interleukin 12 Secretion," *J. Exp. Med.*, 183:693–698 (1996).
PCT Written Opinion dated Nov. 21, 1997, International Application No. PCT/US97/02958.
Padlan, E.A., "A possible procedure for reducing the immunogenicity of antibody variable domains while preserving their ligand–binding properties," *Molecular Immunology*, 28(4/5):489–498 (Apr., 1991).
Hartog et al., "Generation of a humanized anti–CD40 mab for treatment of autoimmune diseases," *Immunotechnology*, 2(4):299 (Nov., 1996) (Abstract).
Fanslow et al., "CD40 mAbs M2 and M3 inhibit CD40L binding and function," *Tissue Antigens*, 42(3):304 (Oct., 1993) (Abstract B022).
Armitage et al., "Molecular and Biological Characterization of a Murine Ligand for CD40", *Nature*, 357:80–82 (May 7, 1992).
Banchereau et al., "Growing Human B Lymphocytes in the CD40 System", *Nature*, 353:678–679 (Oct. 17, 1991).
Banchereau et al., "Long–Term Human B Cell Lines Dependent on Interleukin–4 and Antibody to CD40", *Science*, 251:70–72 (Jan. 4, 1991).
Chothia, et al., "Canonical Structures for the Hypervariable Regions of Immunoglobulins," *J. Mol. Biol.*, 196:901–917 (1987).
Clark and Shu, "Association Between IL–6 and CD40 Signaling IL–6 Induces Phosphorylation of CD40 Receptors", *J. Immunol.*, 145(5):1400–1406 (Sep. 1, 1990).
Clark et al., "Activation of Human B Cells Mediated Through Two Distinct Cell Surface Differentiation Antigens, Bp35 and Bp50", *Proc. Natl. Acad. Sci. USA*, 83:4494–4498 (Jun. 1986).
Cosimi, et al., "Use of Monoclonal Antibodies To T–Cell Subsets for Immunologic Monitoring and Treatment in Recipients of Renal Allografts," *N. Eng. J. Med.*, 305:308–313 (Aug. 6, 19881).
de Boer et al., "Generation of monoclonal antibodies to human lymphocyte cell surface antigens using insect cells expressing recombinant proteins", *J. Immunol. Meth.*, 152:15–23 (1992).
DeFranco et al., "Separate Control of B Lymphocyte Early Activation and Proliferation in Response to Anti–IgM Antibodies", *J. Immunol.*, 135(1):87–94 (Jul. 1985).
DiSanto et al., "Generation of Anti–human CD8β–Specific Antibodies Using Transfectants Expressing Mixed CD8 Heterodimers," *J. Immunol. Meth.*, 141:123–131 (1991).
Freedman et al., "B7, A B Cell–Restricted Antigen that Identifies Preactivated B Cells", *J. Immunol.*, 139(10):3260–3267 (Nov. 15, 1987).

(List continued on next page.)

Primary Examiner—Christina Y. Chan
Assistant Examiner—Phillip Gambel
Attorney, Agent, or Firm—Donald J. Pochopien; Paul B. Savereide; Robert P. Blackburn

[57] ABSTRACT

Methods for preventing or treating an antibody-mediated disease in patient are presented, the methods comprising administration of a humanized monoclonal antibody or fragment thereof that is capable of binding to a human CD40 antigen located on the surface of a human B cell, wherein the binding of the antibody to the CD40 antigen prevents the growth or differentiation of the B cell. Humanized monoclonal antibodies and fragments useful in these methods are also presented.

20 Claims, 18 Drawing Sheets

OTHER PUBLICATIONS

Gascan et al., "Anti–CD40 Monoclonal Antibodies or CD4+ T Cell Clones and IL–4 Induce IgG4 and IgE Switching in Purified Human B Cells Via Different Signaling Pathways", *J. Immunol.*, 147(1):8–13 (Jul. 1, 1991).

Gauchat et al., "Modulation of IL–4 Induced Germline $\epsilon$ RNA Synthesis in Human B Cells by Tumor Necrosis Factor–$\alpha$, Anti–CD40 Monoclonal Antibodies or Transforming Growth Factor–$\beta$ Correlates with Levels of IgE Production", *Int. Immunol.*, 4(3):397–406 (1991).

Golub, "Immunology A Synthesis", published by Sinauer Assoc. Inc., Sunderland, MA, pp. 19–20 (1987).

Gordon et al., "Resting B Lymphocytes Can Be Triggered Directly Through the CDw40 (BP50) Antigen", *J. Immunol.*, 140(5):1425–1430 (Mar. 1, 1988).

Gruber et al., "Anti–CD45 Inhibition of Human B Cell Proliferation Depends on the Nature of Activation Signals and the State of B Cell Activation", *J. Immunol.*, 142(12):4144–4152 (Jun. 15, 1989).

Harris et al., "Therapeutic antibodies—the coming of age", *TIBTECH*, 11(2):42–44 (Feb. 1993).

Jabara et al., "CD40 and IgE: Synergism between Anti–CD40 Monoclonal Antibody and Interleukin 4 in the Induction of IgE Synthesis by Highly Purified Human B Cells", *J. Exp. Med.*, 172:1861–1864 (Dec. 1990).

June et al., "Role of the CD28 Receptor in T–Cell Activation", *Immunology Today*, 11(6):211–216 (1990).

Jung and Fu, "Selective Inhibition of Growth Factor–Dependent Human B Cell Proliferation by Monoclonal Antibody AB1 to an Antigen Expressed by Activated B Cells", *J. Exp. Med.*, 160:1919–1924 (Dec. 1984).

Kabat et al., "Sequences of Proteins of Immunological Interest," Tabulation and Analysis of Amino Acid and Nucleic Acid Sequences of Precursors, V–Regions, C–Regions, J–Chain, $\beta_2$–Microglobulins, Major Histocompatibility Antigens, Thy–1, Complement, C–Reactive Protein, Thymopoietin, Post–gamma Globulin, and $\alpha_2$–Macroglobulin, sponsored through Contract NO1–RR–8–2118 by components of the National Institutes of Health, Bethesda, MD 20205 (1983).

Kriegler et al., "A Novel Form of TNF/Cachectin Is a Cell Surface Cytotoxic Transmembrane Protein: Ramifications for the Complex Physiology of TNF," *Cell*, 53:45–53 (1988).

Kwekkenboom et al., "CD40 plays an essential role in the activation of human B cells by murine EL4B5 cells", *Immunology*, 79:439–444 (1993).

Lane et al., "Activated human T cells express a ligand for the human B cell–associated antigen CD40 which participated in T cell–dependent activation of B lymphocytes", *Eur. J, Immunol.*, 22:2573–2578 (1992).

Ledman et al., "Anti–CD40 Monoclonal Antibody Blocks the Contact Dependent T Helper Signal Mediated by 5C8 Ag.", *Clinical Research*, 40:154A (1992).

Linsley et al., "CTLA–4 Is a Second Receptor for the B Cell Activation Antigen B7", *J. Exp. Med.*, 174:561–569 (Sep. 1991).

Muraguchi et al., "Sequential Requirements for Cell Cycle Progression of Resting Human B Cells After Activation by Anti–Ig", *J. Immunol.*, 132(1):176–180 (1984).

Noell and Snow, "T helper cells", *Current Opinion in Immunology*, 4:333–337 (1992).

Paulie et al., "The Human B Lymphocyte and Carcinoma Antigen, CDw40, Is a Phosphoprotein Involved in Growth Signal Transducion", *J. Immunol.*, 142(2):590–595 (Jan. 15, 1989).

Ross et al., "Characterization of nerve growth factor in neural crest tumors using monoclonal antibodies", *Proc. Natl. Acad. Sci. USA*, 81:6681–6685 (Nov. 1984).

Rousset et al., "Cytokine–induced Proliferation and Immunoglobulin Production of Human B Lymphocytes Triggered Through Their CD40 Antigen", *J. Exp. Med.*, 173:705–710 (Mar. 1991).

Sato et al., "Biological Effects in Vitro of Monoclonal Antibodies to Human Epidermal Growth Factor Receptors", *Mol. Biol. Med.*, 1:511–529 (1983).

Splawski et al., "Immunoregulatory Role of CD40 in Human B Cell Differentiation", *J. Immunol.*, 150(4):1276–1285 (Feb. 15, 1993).

Tanaka et al., "Distinct Reactivities of Four Monoclonal Antibodies with Human Interleukin 2 Receptor", *Microbiol. Immunol.*, 29(10):959–972 (1985).

Uckun et al., "Temporal Association of CD40 Antigen Expression with Discreet Stages of Human B–Cell Ontogeny and the Efficacy of Anti–CD40 Immunotoxins Against Clonogenic B–Lineage Acute Lymphoblastic Leukemia as well as B–Lineage Non–Hodgkin's Lymphoma Cells", *Blood*, 76(12):2449–2456 (Dec. 15, 1990).

Valle et al., "mAb 104, A New Monoclonal Antibody, Recognizes the B7 antigen that is Expressed on Activated B Cells and HTLV–1–Transformed T Cells", *Immunology*, 69:531–535 (1990).

Webb, "Cell–surface Expression And Proliferation of Human CD4 Produced in Baculovirus–Infected Insect Cells", *Proc. Natl. Acad. Sci. USA*, 86:7731–7735 (Oct. 1989).

Wetzel et al., "Evidence for Two Distinct Activation States Available to B Lymphocytes", *J. Immunol.*, 133(5):2327–2332 (Nov. 1984).

Yellin et al., "CD40 Molecules Induce Down–Modulation and Endocytosis of T Cell Surface T Cell–B Activating Molecule/CD40–L", *J. Immunol.*, 152:598–608 (1994).

Zhang et al., "CD40 Stimulation Provides an IFN–$\gamma$ Independent and IL–4–Dependent Differentiation Signal Directly to Human B Cells For IgE Production", *J. Immunol.*, 146(6):1836–1842 (Mar. 15, 1991).

Francisco et al. Cancer Research 55: 3099–3104 (1995).

Paul (ED) Fundamental Immunology Raven Press NY 1993, p. 242 only.

Kahan Curr. Opin Immunology 4: 553–560 (1992).

Edgington Biotechnology 10: 383–389 (1992).

Ward et al. Therapeutic Immunology 1: 165–171 (1994).

Classen et al. J. Allergy Clin. Immunol. 88: 713–721 (1991).

Knight et al. Mol. Immunol. 32 :1271–1281 (1995).

PCT International Search Report Dated Jun. 23, 1997, International Application PCT/US97/02858.

Full length B7:

Forward MR67 5'-GCG CTGCAG CATCTGAAGCCATGGGCC-3' (307-324)

Backward MR68 5'-CGC GGTACC TTGCTTCTGCGGACACTG-3' (1182-1199)

Soluble B7:

Forward MR67 5'-GCG CTGCAG CATCTGAAGCCATGGGCC-3' (307-324)

Backward MR145 5'-GCGC GGTACC TTACTCCATGGGCATGTATTCCTTCTTCCTGTTATCAGGAAAATGCTGTTG-3' (1022-1042)

Full length CD40:

Forward MR108 5'-GCGT AGATCT GGTCTCACCTGCCATGGTTCG-3' (34-55)

Backward MR112 5'-GCGT GGTACC CCACACTCCTGGGTGGGTGCAGCC-3' (882-905)

Soluble CD40:

Forward MR108 5'-GCGT AGATCT GGTCTCACCTGCCATGGTTCG-3' (34-55)

Backward MR150 5'-GCGT GGTACC TTACTCCATGGGCATGTATTCCTTCTTCCTCATCAGTCTTGTTGTGCCTGC-3' (575-596)

```
FR1
  1 GAG CTC CAG CTG ACC CAG TCT CCA CTC TCC CTG CCT GTC AGT CTT GGA  48
  1  E   L   Q   L   T   Q   S   P   L   S   L   P   V   S   L   G  16
                                 CDR1
 49 GAT CAA GCC TCC ATC TCT TGC AGA TCT AGT CTG CAG AGC CTT GTA AAC AGT  96
 17  D   Q   A   S   I   S   C   R   S   S   L   Q   S   L   V   N   S  32
                             FR2
 97 AAT GGA AAC ACC TAT TTA CAT TGG TAC CTG CAG AAG CCA GGC CAG TCT 144
 33  N   G   N   T   Y   L   H   W   Y   L   Q   K   P   G   Q   S  48
                 CDR2                                        FR3
145 CCA AAG CTC CTC ATC TAC AAA GTT TCC AAC CGA TTT TCT GGG GTC CCA 192
 49  P   K   L   L   I   Y   K   V   S   N   R   F   S   G   V   P  64
193 GAC AGG TTC AGT GGC AGT GGA TCA GGG ACA GAT TTC ACA CTC AAG ATC 240
 65  D   R   F   S   G   S   G   S   G   T   D   F   T   L   K   I  80
241 AGC AGA GTG GAG GCT GAG GAT CTG GGA GTT TAT TTC TGC TCT CAA AGT 288
 81  S   R   V   E   A   E   D   L   G   V   Y   F   C   S   Q   S  96
                     FR4                                CDR3
289 ACA CAT GTT CCG TGG ACG TTC GGT GGA GGC ACC AAG CTG GAA ATC AAA 336
 97  T   H   V   P   W   T   F   G   G   G   T   K   L   E   I   K 112
```

FIG. 11

```
FR1
  1 CAG GTG CAA CTC GTG GAG TCT GGA CCT GGC CTG GTG AAA CCC TCA CAG         48
  1  Q   V   Q   L   V   E   S   G   P   G   L   V   K   P   S   Q         16
                                                                  CDR1
 49 AGC CTG TCC ATC ACA TGC ACT GTC TCT GGG TTC TCA TTA TCC TCC AGA TAT     96
 17  S   L   S   I   T   C   T   V   S   G   F   S   L   S   S   R   Y     32
              FR2
 97 AGT GTA TAC TGG GTT CGC CAG CCT CCA GGA AAG GGT CTG GAG TGG CTG        144
 33  S   V   Y   W   V   R   Q   P   P   G   K   G   L   E   W   L         48
        CDR2
145 GGA ATG ATG TGG GGT GGA GGA ACA GAC TAT AAT TCA GCT CTC AAA            192
 49  G   M   M   W   G   G   G   T   D   Y   N   S   A   L   K             64
        FR3
193 TCC AGA CTG ACC ATC AGC AAG GAC AAG TCG AAG GCC AAC CAG TTC TTC TTA    240
 65  S   R   L   T   I   S   K   D   K   S   K   A   N   Q   F   F   L     80
241 AAA ATG AAC AGT CTG CGA GAG GCT ACA GCC ATG TAC TAC TGT GTC            288
 81  K   M   N   S   L   R   E   A   T   A   M   Y   Y   C   V             96
        CDR3                       FR4
289 AGA ACC GAT GGG GAC TAC TGG GGT CAA GGA ACC ACC GTC ACC GTC TCC        336
 97  R   T   D   G   D   Y   W   G   Q   G   T   T   V   T   V   S        112
337 TCA                                                                    339
113  S                                                                    113
```

```
     FR1
  1  GAC CTC CAG CTG ACC CAG TCT CCA CTC TCC CTG CCT GTC AGT CTT GGA   48
  1   D   L   Q   L   T   Q   S   P   L   S   L   P   V   S   L   G   16

CDR1
 49  GAT CGA GCC TCC ATC TCT TGC AGA TCT AGT CAG AGC CTT GTA AAC AGT   96
 17   D   R   A   S   I   S   C   R   S   S   Q   S   L   V   N   S   32

FR2                      CDR2
 97  AAT GGA AAC ACC TAT TTA CAT TGG TAC CTG CAG AAG CCA GGC CAG TCT  144
 33   N   G   N   T   Y   L   H   W   Y   L   Q   K   P   G   Q   S   48

CDR2
145  CCA AAG CTC CTG ATC TAC AAA GTT TCC AAC CGA TTT TCT GGG GTC CCA  192
 49   P   K   L   L   I   Y   K   V   S   N   R   F   S   G   V   P   64

FR3
193  GAC AGG TTC AGT GGC AGT GGA TCA GGG ACA GAT TTC ACA CTC AAG ATC  240
 65   D   R   F   S   G   S   G   S   G   T   D   F   T   L   K   I   80

CDR3
241  AGC AGA GTG GAG GCT GAG GAT CTG GGA GTT TAT TAC TGC TCT CAA AGT  288
 81   S   R   V   E   A   E   D   L   G   V   Y   Y   C   S   Q   S   96

FR4
289  ACA CAT GTT CCG TGG ACG TTC GGT GGA GGC ACC AAG CTG GAA ATC AAA  336
 97   T   H   V   P   W   T   F   G   G   G   T   K   L   E   I   K  112
```

HUMANIZED ANTI-CD40 MONOCLONAL ANTIBODIES AND FRAGMENTS CAPABLE OF BLOCKING B CELL PROLIFERATION

CROSS-REFERENCE TO RELATED APPLICATIONS

This application is a continuation-in-part of U.S. Ser. No. 08/070,158, filed May 28, 1993 U.S. Pat. No. 5,677,165 now, which is a continuation-in-part of U.S. Ser. No. 07/910,222 filed Jul. 9, 1992, now U.S. Pat. No. 5,397,703, the disclosures of which are hereby incorporated by reference.

FIELD OF THE INVENTION

This invention relates to antibodies and methods for treating diseases of the immune system. In particular, this invention relates to humanized anti-CD40 antibodies and methods of preventing or treating antibody-mediated diseases such as IgE-mediated disease (allergies) and autoimmune diseases including systemic lupus erythematosus (SLE), primary biliary cirrhosis (PBC), idiopathic thrombocytopenic purpura (ITP), and rheumatoid arthritis (RA).

BACKGROUND OF THE INVENTION

I. B-Cell Activation

B cells play an important role during the normal in vivo immune response. A foreign antigen will bind to surface immunoglobulins on specific B cells, triggering a chain of events including endocytosis, processing, presentation of processed peptides on MHC-class II molecules, and up-regulation of the B7 antigen on the B-cell surface. A specific T cell then binds to the B cell via T-cell receptor (TCR) recognition of processed antigen presented on the MHC-class II molecule. Stimulation through the TCR begins to activate the T cell and initiates T-cell cytokine production. Interaction between the CD28 antigen on T cells and the B7 antigen on B cells can provide a second signal further activating the T cell, resulting in high level cytokine secretion. Additionally, the CD40 ligand, which is not expressed on resting human T cells, is up-regulated on the T-cell surface when the above-mentioned signals are received. The B cell is then stimulated by The CD40 ligand through the CD40 antigen on the B-cell surface, and also by soluble cytokines, causing the B cell to mature into a plasma cell secreting high levels of soluble immunoglobulin.

II. The EL4B5 Cell Line

A few years ago, Zubler et al., *J. Immunol.* (1985) 134:3662, observed that a mutant subclone of the mouse thymoma EL-4 line, known as EL4B5, could strongly stimulate B cells of both murine and human origin to proliferate and differentiate into immunoglobulin-secreting plasma cells in vitro. This activation was found to be antigen-independent and not MHC restricted. For optimal stimulation of human B cells, the presence of supernatant from activated human T cells was needed, but a B-cell response also occurred when EL4B5 cells were preactivated with phorbol-12-myristate 13-acetate (PMA) or IL-1. Zubler et al., (*Immunological Reviews* (1987) 99:281; and Zhang et al., *J. Immunol.* (1990) 144:2955. B-cell activation in this culture system is efficient—limiting dilution experiments have shown that the majority of human B cells can be activated to proliferate and differentiate into antibody-secreting cells. Wen et al., *Eur. J. Immunol.* (1987) 17:887.

The mechanism by which these mutant EL-4 cells activate both murine and human B cells has not been elucidated previously. It is, however, clear that cell-cell contact is required for EL4B5-induced B-cell activation. First, B cells do not proliferate in the presence of supernatant from PMA-stimulated EL4B5 cells. Zubler et al. (1985) supra. Second, B cells do not proliferate when they are separated from PMA-treated EL4B5 cells by a semipermeable filter membrane. Zhang et al., supra. Antibodies against mouse LFA-1, human LFA-1 or human LFA-3 and antibodies against mouse or human MHC class II molecules do not inhibit EL4B5-induced proliferation of human or murine B cells. Zubler et al. (1987) and Zhang et al., supra.

III. The CD40 Antigen, the CD40 Antigen Ligand, and Anti-CD40 Antibodies

The CD40 antigen is a glycoprotein expressed on the cell surface of B cells. During B-cell differentiation, the molecule is first expressed on pre-B cells and then disappears from the cell surface when the B cell becomes a plasma cell. Crosslinking of the CD40 molecules with anti-CD40 antibodies mediates a variety of effects on B cells. The CD40 antigen is known to be related to the human nerve growth factor (NGF) receptor and tumor necrosis factor-alpha (TNF-$\alpha$) receptor, suggesting that CD40 is a receptor for a ligand with important functions in B-cell activation.

A ligand for CD40 has been identified on the cell surface of activated T cells. Fenslow et al., *J. Immunol.* (1992) 149:655 Lane et al., *Eur. J. Immunol.* (1992) 22:2573; Noelle et al. *Proc. Natl. Acad. Sci.* (USA) (1992) 89:6550. cDNA cloning of the CD40 ligand revealed a molecule with characteristics of a type-II transmembrane glycoprotein with homology to TNF-$\alpha$. Armitage et al., *Nature* (1992) 357:80 and Spriggs et al., *J. Exp. Med.* (1992) 176:1543. The extracellular domain of the CD40 ligand contains two arginine residues proximal to the transmembrane region, providing a potential proteolytic cleavage site that could give rise to a soluble form of the ligand. Expression of recombinant CD40 ligand has demonstrated that this molecule can stimulate the proliferation of purified B cells and, in combination with IL-4, mediate the secretion of IgE. Armitage et al. and Spriggs et al., supra. It has been reported that abnormalities in the gene for the CD40 ligand, resulting in the absence of a functional molecule on activated T cells, is responsible for the occurrence of X-linked hyper-IgM syndrome, a rare disorder characterized by the inability of these patients to produce normal levels of antibody isotypes other than IgM. Allen et al., *Science* (1993) 259:990; and Korthäuer et al., *Nature* (1993) 361:539.

All anti-CD40 antibodies known in the art have a stimulatory effect on human B cells. Cross-linking of the CD40 molecule on the B-cell surface using known anti-CD40 antibodies mediates a variety of effects on B cells. Anti-CD40 monoclonal antibodies (mAbs) can induce intercellular adhesion, proliferation and, in combination with certain cytokines, maturation to antibody secreting cells. For example, known anti-CD40 mAbs have been shown to mimic the effects of T helper cells in B-cell activation. When presented on adherent cells expressing Fc$\gamma$RII, these antibodies induce B-cell proliferation. J. Bancereau et al., *Science* (1989) 251:70. Moreover, the known anti-CD40 mAbs can replace the T helper signal for secretion of IgM, IgG and IgE in the presence of IL-4. H. Gascan et al., *J. Immunol.* (1991) 147:8. Furthermore, known anti-CD40 mAbs can prevent programmed cell death (apoptosis) of B cells isolated from lymph nodes.

However, the anti-CD40 antibodies known in the art stimulate B cells but are incapable of inhibiting the B-cell response. Furthermore, no anti-CD40 antibodies are known that are (1) capable of inhibiting the B-cell response and (2) that can be used to prevent or treat antibody-mediated disease.

SUMMARY OF THE INVENTION

The current invention is based on the discovery of anti-CD40 antibodies that do not stimulate the growth and differentiation of human B cells. In contrast, these antibodies can inhibit the human B-cell response at relatively low concentrations. Accordingly, these antibodies can be used to prevent or treat diseases or conditions that are mediated by antibodies produced by the human B-cell response. These antibodies also recognize novel epitopes on the CD40 antigen useful in modulating the B-cell response.

Accordingly, the present invention is directed to providing a monoclonal antibody or an antigen binding fragment thereof capable of binding to a human CD40 antigen located on the surface of a human B cell, wherein the binding of the antibody or fragment to the CD40 antigen prevents the growth or differentiation of the B cell, the humanized monoclonal antibody having an effective number of exposed amino acid residues in its framework regions that are consistent with the amino acid residues usually found in the corresponding framework regions of a human antibody to provide a reduced immunogenicity in humans. Hereinafter, it is understood that the term "monoclonal antibody," as used in the context of the anti-CD40 monoclonal antibodies of the claimed invention, includes antigen binding fragments thereof.

The present invention is also directed to providing a method for preventing or treating an antibody-mediated disease in a patient, the method comprising administering to a patient in need of such treatment a composition comprising: (i) a therapeutically effective amount of a monoclonal antibody (or fragment thereof) that is capable of binding to a human CD40 antigen located on the surface of a human B cell, wherein the binding of the antibody to the CD40 antigen prevents the growth or differentiation of the B cell, the antibody having an effective number of exposed amino acid residues in its framework region that are consistent with the amino acid residues usually found in the corresponding antibody to provide a reduced immunogencity in humans, and (ii) a pharmaceutically acceptable excipient.

In another aspect, the present invention is directed to providing a method for preventing or treating an IgE-mediated disease such as an allergy in a patient, the method comprising administering to a patient in need of such treatment a therapeutically effective amount of a monoclonal antibody (or fragment thereof) that is capable of binding to a human CD40 antigen located on the surface of a human B cell, wherein the binding of the antibody to the CD40 antigen prevents the growth or differentiation of the B cell, the antibody being in a pharmaceutically acceptable excipient.

Further, the present invention is directed to providing a method for preventing or treating an antibody-mediated autoimmune disease in a patient, the method comprising administering to a patient in need of such treatment a therapeutically effective amount of a monoclonal antibody (or a fragment thereof) capable of binding to a human CD40 antigen located on the surface of a human B cell, wherein the binding of the antibody to the CD40 antigen prevents the growth or differentiation of the B cell, in a pharmaceutically acceptable excipient. Particular autoimmune diseases contemplated for treatment by this method include systemic lupus etythematosus (SLE), primary biliary cirrhosis (PBC), idiopathic thrombocytopenic purpura (ITP), and rheumatoid arthritis (RA).

It is a further object of this invention to provide a CD40 antigen epitope capable of competing with the binding of a CD40 antigen to an anti-CD40 monoclonal antibody wherein the binding of that antibody to a human CD40 antigen located on the surface of a human B cell prevents the growth or differentiation of the B cell.

In preferred embodiments of the above methods, the monoclonal antibody is either 5D12, 3A8 or 3C6. In a more preferred embodiment, the anti-CD40 monoclonal antibody or fragment thereof has been humanized by comparing the amino acid sequence of the monoclonal antibody to the amino acid sequences of several of the most homologous human antibodies and performing site directed mutagenesis by changing the amino acids in the framework regions of the variable regions which are exposed and which do not match up with their human counterparts. Such humanized antibodies are preferred because they are less likely to invoke an immune response in humans. In a particularly preferred embodiment, the anti-CD40 monoclonal antibody is a humanized CDR fragment of an anti-CD40 monoclonal antibody that is capable of binding to the CD40 antigen.

BRIEF DESCRIPTION OF THE DRAWINGS

FIG. 2 shows the sequences of polymerase chain reaction primers used in the preparation of coding regions for human CD40 and human B7 antigens. These primers were constructed on the basis of the published complete DNA coding sequences for antigens B7 and CD40.

FIG. 10 shows the DNA sequence for the murine heavy chain variable ($VH_M$) region of the 5D12 monoclonal antibody and the amino acid sequence encoded thereby, using conventional single letter designations. FIG. 10 also labels $VH_M$ at the first amino acid of each of the four framework regions (FR1, FR2, FR3 and FR4) and the three complementarity determining regions (CDR1, CDR2, CDR3) that are positioned therebetween in alternating fashion.

FIG. 11 shows the DNA sequence for the murine light chain variable ($VL_M$) region of the 5D12 monoclonal antibody and the amino acid sequence encoded thereby, using conventional single letter designations. FIG. 11 also labels $VL_M$ the first amino acid of each of the four framework regions (FR1, FR2, FR3 and FR4) and the three complementarity determining regions (CDR1, CDR2 and CDR3) that are positioned therebetween in alternating fashion.

FIG. 12 shows the DNA sequence for the humanized heavy chain variable (VH$_x$) region of 5D12 monoclonal antibody and the amino acid sequence encoded thereby, using conventional single letter designations. FIG. 12 also labels VH$_x$ the first amino acid of each of the four framework regions (FR1, FR2, FR3 and FR4) and the three complementarity determining regions (CDR1, CDR2 and CDR3) that are positioned therebetween in alternating fashion.

FIG. 13 shows the DNA sequence for the humanized light chain variable (VL$_x$ region of the 5D12 monoclonal antibody and the amino acid sequence encoded thereby, using conventional single letter designations. FIG. 13 also labels VL$_x$ at the first amino acid residue of each of the four framework regions (FR1, FR2, FR3 and FR4) and the three complementarity determining regions (CDR1, CDR2 and CDR3) that are positioned therebetween in alternating fashion.

FIG. 14 shows that chimeric 5D12 Fab and humanized 5D12 Fab exhibit the same binding to CD40 expressing cells as does the intact 5D12 monoclonal antibody.

DETAILED DESCRIPTION OF INVENTION

Figure 1A:
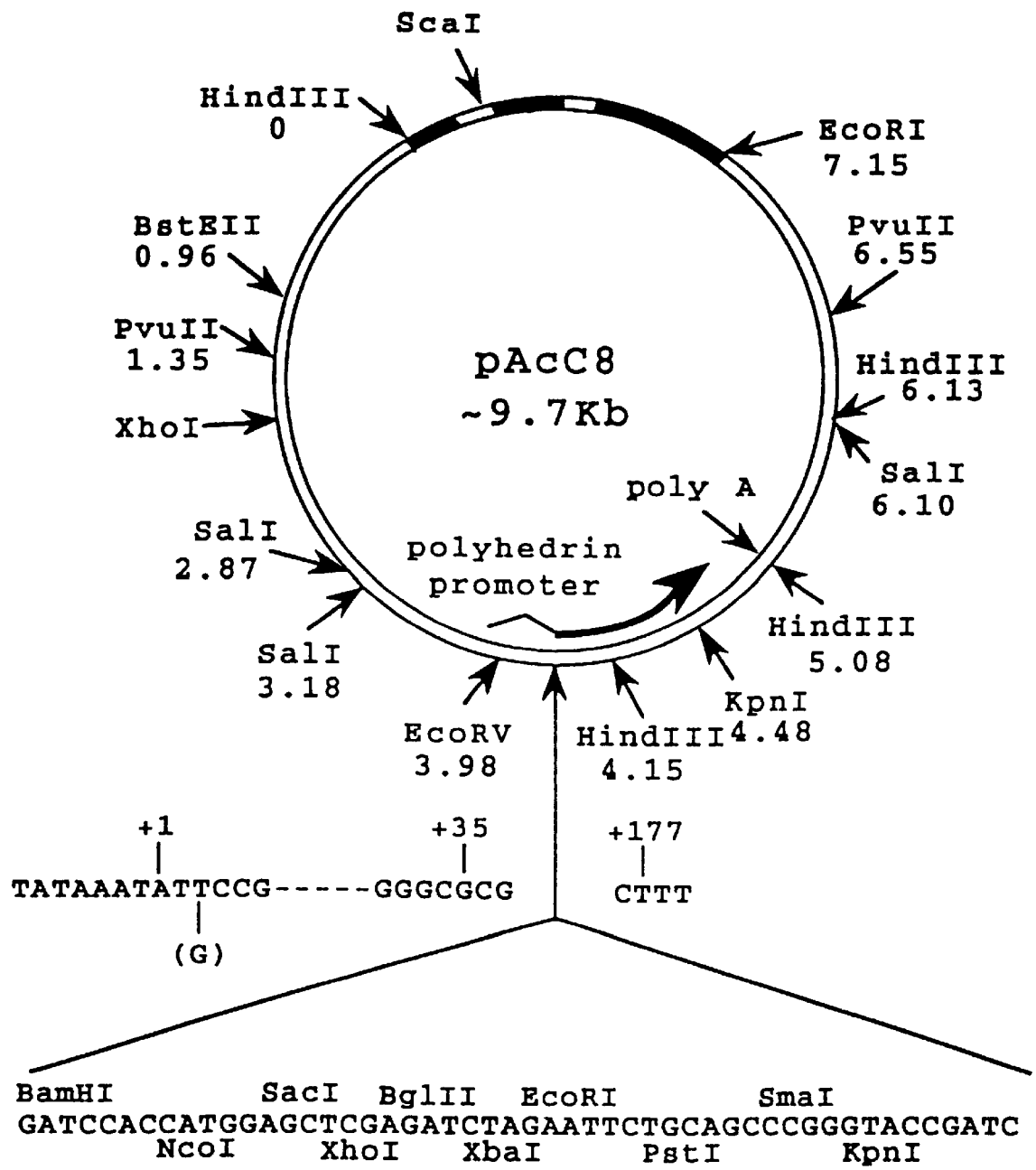
FIG. 1A shows a schematic representation of the baculoviral transfer vector pAcC8 and the sequence of the multiple cloning site.

The invention described herein draws on previously published work and pending patent applications. By way of example, such work consists of scientific papers, patents or pending patent applications. All of these publications and applications, cited previously or below are hereby incorporated by reference.

Definitions:

As used herein, the term "antibody" refers to polyclonal antibodies, monoclonal antibodies, humanized antibodies, single-chain antibodies, and fragments thereof such as F$_{ab}$, F$_{(ab')2}$, F$_v$, and other fragments, such as CDR fragments, which retain the antigen binding function of the parent antibody.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as F$_{ab}$, F$_{(ab')2}$, F$_v$, and others, such as CDR fragments, which retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "humanized monoclonal antibodies" means that at least a portion of the exposed amino acids in the framework regions of the antibody (or fragment), which do not match with the corresponding amino acids in the most homologous human counterparts, are changed, such as by site directed mutagenesis of the DNA encoding the antibody. Because these exposed amino acids are on the surface of the molecule, this technique is called "resurfacing." Moreover, because the amino acids on the surface of the molecule are the ones most likely to give rise to an immune response, this resurfacing decreases the immunogenicity of the monoclonal antibody when administered to a species whose cell line was not used to generate the antibody, such as a human. The term "humanized monoclonal antibody" also includes chimeric antibody wherein the light and heavy variable regions of a monoclonal antibody generated by a hybridoma from a non-human cell line are each attached, via recombinant technology, to one human light chain constant region and at least one heavy chain constant region, respectively. The preparation of such chimeric (i. e., humanized) antibodies are disclosed by references incorporated herein by reference.

As used herein, the term "single chain antibodies" refers to antibodies prepared by determining the binding domains (both heavy and light chains) of a binding antibody, and supplying a linking moiety which permits preservation of the binding function. This forms, in essence, a radically abbreviated antibody, having only that part of the variable domain necessary for binding to the antigen. Determination and construction of single chain antibodies are described in U.S. Pat. No. 4,946,779 to Ladner et al., which is expressly incorporated herein by reference.

The term "CD40 antigen epitope" as used herein refers to molecule which is capable of immunoreactivity with the anti-CD40 monoclonal antibodies of this invention, excluding the CD40 antigen itself. CD40 antigen epitopes may comprise proteins, protein fragments, peptides, carbohydrates, lipids, and other molecules, but for the purposes of the present invention are most commonly proteins, short oligopeptides, oligopeptide mimics (i. e., organic compounds which mimic the antibody binding properties of the CD40 antigen), or combinations thereof. Suitable oligopeptide mimics are described, inter alia, in PCT application US91/04282.

I. Antibody Preparation

Anti-CD40 monoclonal antibodies 5D12, 3A8 and 3C6 were prepared as described in Example 1 herein. Humanized anti-CD40 monoclonal antibody fragments were prepared as described in Example 8. Other monoclonal antibodies of the invention may be prepared similarly, or as follows.

a) Polyclonal Sera

Polyclonal sera may be prepared by conventional methods. In general, a solution containing the CD40 antigen is first used to immunize a suitable animal, preferably a mouse, rat, rabbit, or goat. Rabbits and goats are preferred for the preparation of polyclonal sera due to the volume of serum obtainable, and the availability of labeled anti-rabbit and anti-goat antibodies. Immunization is generally performed by mixing or emulsifying the antigen-containing solution in saline, preferably in an adjuvant such as Freund's complete adjuvant, and injecting the mixture or emulsion parenterally (generally subcutaneously or intramuscularly). A dose of 50–200 μg/injection is typically sufficient. Immunization is generally boosted 2–6 weeks later with one or more injections of the protein in saline, preferably using Freund's incomplete adjuvant. One may alternatively generate antibodies by in vitro immunization using methods known in the art, which for the purposes of this invention is considered equivalent to in vitro immunization.

Polyclonal antisera are obtained by bleeding the immunized animal into a glass or plastic container, incubating the blood at 25° C. for one hour, followed by incubating at 4° C. for 2–18 hours. The serum is recovered by centrifugation (e.g., 1,000×g for 10 minutes). About 20–50 ml per bleed may be obtained from rabbits.

b) Monoclonal Antibodies

Monoclonal antibodies are prepared using the method of Kohler and Milstein, *Nature* (1975) 256:495–96, or a modification thereof, as are well known to the art. Typically, a mouse or rat is immunized as described above. However, rather than bleeding the animal to extract serum, the spleen (and optionally several large lymph nodes) are removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the desired immunizing cell-surface antigen (and which do not bind to unrelated antigens). The selected mAb-secreting hybridomas are then cultured either in witro (e.g., in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a mAb. Further, one may combine various labels for desired effect. For example, mAbs and avidin also require labels in the practice of this invention; thus, one might label a mAb with biotin, and detect its presence with avidin labeled with $^{125}I$, or with an anti-biotin mAb labeled with HRP. Other permutations and possibilities will be readily apparent to those of ordinary skill in the art, and are considered as equivalents within the scope of the instant invention.

CD40 Antigen Epitopes

The CD40 antigen epitopes of this invention are molecules that are immunoreactive with anti-CD40 monoclonal antibodies whose binding to a human CD40 antigen located on the surface of a human B cell prevents the growth of differentiation of the B cell. That is, such epitopes compete with the binding of said antibodies to the CD40 antigen. Systematic techniques for identifying these epitopes are known in the art, as described by H. M. Geysen in U.S. Pat. No. 4,708,871, which is incorporated herein by reference. Typically, these epitopes are short amino acid sequences. These sequences may be embedded in the sequence of longer peptides or proteins, as long as they are accessible.

The epitopes of the invention may be prepared by standard peptide synthesis techniques, such as solid-phase synthesis. Alternatively, the sequences of the invention may be incorporated into larger peptides or proteins by recombinant methods. This is most easily accomplished by preparing a DNA cassette which encodes the sequence of interest, and ligating the cassette into DNA encoding the protein to be modified at the appropriate site. The sequence DNA may be synthesized by standard synthetic techniques, or may be excised from the phage pIII gene using the appropriate restriction enzymes.

Epitopes identified herein may be prepared by simple solid-phase techniques. The minimum binding sequence may be determined systematically for each epitope by standard methods, for example, employing the method described by H. M. Geysen, U.S. Pat. No. 4,708,871. Briefly, one may synthesize a set of overlapping oligopeptides derived from the CD40 antigen bound to a solid phase array of pins, with a unique oligopeptide on each pin. The pins are arranged to match the format of a 96-well microtiter plate, permitting one to assay all pins simultaneously, e.g., for binding to an anti-CD40 monoclonal antibody. Using this method, one may readily determine the binding affinity for every possible subset of consecutive amino acids.

Analogs of the invention are also prepared by standard solid-phase methods, and those methods described in PCT application US91/04282.

Formulations and Methods of Administration

The antibodies of this invention are administered at a concentration that is therapeutically effective to prevent or treat antibody-mediated diseases such as allergies, SLE, PBC, ITP and RA. To accomplish this goal, the antibodies may be formulated using a variety of acceptable excipients known in the art. Typically, the antibodies are administered by injection, either intravenously or intraperitoneally. Methods to accomplish this administration are known to those of ordinary skill in the art. It may also be possible to obtain compositions which may be topically or orally administered, or which may be capable of transmission across mucous membranes.

Before administration to patients, formulants may be added to the antibodies. A liquid formulation is preferred. For example, these formulants may include oils, polymers, vitamins, carbohydrates, amino acids, salts, buffers, albumin, surfactants, or bulking agents. Preferably carbohydrates include sugar or sugar alcohols such as mono-, di- or polysaccharides, or water soluble glucans. The saccharide or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylellulose, or mixtures thereof. Sucrose is most preferred. "Sugar alcohol" is defined as a $C_4$ to $C_8$ hydrocarbon having an —OH group and includes galacitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of canitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Most preferred is a citrate buffer. Preferably, the concentration is from 0.01 to 0.3 molar. Surfactants that can be added to the formulation are shown in EP Nos. 270,799 and 268,110.

Additionally, antibodies can be chemically modified by covalent conjugation to a polymer to increase their circulating half-life, for example. Preferred polymers, 4,179,337; 4,495,285; and 4,609,546 which are all hereby incorporated by reference in their entireties. Preferred polymers are polyoxyethylated polyols and polyethylene glycol (PEG). PEG is soluble in water at room temperature and has the general formula: $R(O-CH_2-CH_2)_nO-R$ where R can be hydrogen, or a protective group such as an alkyl or aklanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1,000 and 40,000, more preferably between 2,000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/antibody of the present invention.

Water soluble polyoxyethylated polyols are also useful in the present invention. They include polyoxyethylated sorbitol, polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di- and triglycerides. Therefore, this branching would not necessarily be seen as a foreign agent in the body. The POG has a preferred molecular weight in the same range as PEG. The structure for POG is shown in Knauf et al., 1988 *J. Bio. Chem.* 263:15064–15070, and a discussion of POG/IL-2 conjugates is found in U.S. Pat. No. 4,766,106, both of which are hereby incorporated by reference in their entireties.

Another drug delivery system for increasing circulatory half-life is the liposome. Methods of preparing liposome delivery systems are discussed in Gabizon et al., *Cancer Research* (1982) 42:4734; Cafiso, *Biochem. Biophys. Acta* (1981) 649:129; and Szoka, *Ann. Rev. Biophys. Eng.* (1980) 9:467. Other drug delivery systems are known in the art and are described in e.g., Poznansky et al., DRUG DELIVERY SYSTEMS (R. L. Juliano, Ed., Oxford, N.Y. 1980), pp. 253–315; M. L. Poznansky, *Pharm. Revs.* (1984) 36:277.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

As stated above, the antibodies and compositions of this invention are used to treat human patients to prevent or treat antibody-mediate diseases such as allergies, SLE, PBC, ITP and RA. The preferred route of administration is parenterally. In parenteral administration, the compositions of this invention will be formulated in a unit dosage injectable form such as a solution, suspension or emulsion, in association with a pharmaceutically acceptable parenteral vehicle. Such vehicles are inherently nontoxic and nontherapeutic. Examples of such vehicles are saline, Ringer's solution, dextrose solution, and Hanks' solution. Nonaqueous vehicles such as fixed oils and ethyl oleate may also be used. A preferred vehicle is 5% dextrose in saline. The vehicle may contain minor amounts of additives such as substances that enhance isotonicity and chemical stability, including buffers and preservatives.

The dosage and mode of administration will depend on the individual. Generally, the compositions are administered so that antibodies are given at a dose between 1 $\mu$g/kg and 20 mg/kg, more preferably between 20 $\mu$g/kg and 10 mg/kg, most preferably between 1 and 7 mg/kg. Preferably, it is given as a bolus dose, to increase circulating levels by 10–20 fold and for 4–6 hours after the bolus dose. Continuous infusion may also be used after the bolus dose. If so, the antibodies may be infused at a dose between 5 and 20 $\mu$g/kg/minute, more preferably between 7 and 15 $\mu$g/kg/minute.

The present invention will now be illustrated by reference to the following examples which set forth particularly advantageous embodiments. However, it should be noted that these embodiments are illustrative and are not to be construed as restricting the invention in any way.

EXAMPLES

Materials and Methods

Cell Lines

The mutant mouse thymoma EL-4 subclone EL4B5 was a gift of Dr. R. H. Zubler, Hôpital Cantonal Universitaire, Geneva. Mouse 3T6 transfectant cells expressing hybrid molecules of the HR (high responder) allelic form of human F$\gamma$RIIa were a gift of Dr. P. A. M. Warmerdam, Department of Experimental Immunology, University Hospital Utrecht, Utrecht, The Netherlands. Warmerdam et al., *J. Immunol.* (1991) 147:1338. Both cell lines were cultured in Iscove's Modified Dulbecco's Medium (IMDM), supplemented with gentamicin (80 $\mu$g/ml) and 10% heat-inactivated fetal calf serum (FCS) (Hyclone, Logan, Utah). To avoid possible loss of B Cell activating capacity, every 4 to 8 weeks a new batch of EL4B5 cells was thawed. The cell lines were periodically tested for mycoplasma contamination by the use of a $^3$H-labelled DNA probe for mycoplasma ribosomal RNA (GenProbe, San Diego, Calif.) and were free of mycoplasma during the course of the experiments.

Antibodies and hCD40.h$\mu$ Fusion Protein

Anti-CD40 mAb 5D12, 3C6 and 3A8 were generated by immunizing mice with insect cells expressing recombinant human CD40 as shown in Example 1. Anti-(B7) mAb B7-24 was generated in a similar way by immunizing with insect cells expressing recombinant human B7. Anti-CD40 mAb S2C6 was a gift of Dr. S. Pauli (University of Stockholm, Sweden). Pauli et al., *J. Immunol.* (1989) 142:590. Anti-CD40 mAb G28.5 was donated by Dr. J. A. Ledbetter (Oncogen Corporation, Seattle, Wash., USA). Clark et al., PNAS (USA) (1986) 83:4494. Control antibodies were: anti-(β-glucocerebrosidase) mAb 8E4 (IgG1), Barneveld et al., *Eur. J. Biochem.* (1983) 134:585, and myeloma immunoglobulins MOPC-21 (IgG1) and MOPC-141 (IgG2b) (Sigma, St. Louis, Mo.). All mAb were used as purified antibody preparations. hCD40.hμ fusion protein was a gift of Dr. P. Lane (Basel Institute for Immunology, Basel, Switzerland) and was used as a 5× concentrated supernatant of transfected J558L cells. Lane et al., *Eur. J. Immunol.* (1992) 22:2573.

Human B Lymphocytes

B lymphocytes were isolated from tonsils obtained from children undergoing tonsillectomies, essentially as described in De Groot et al., *Lymphokine Research* (1990) 9:321. Briefly, the tissue was dispersed with scalpel blades, phagocytic and NK cells were depleted by treatment with 5 mM L-leucine methyl ester and T cells were removed by one cycle of rosetting with sheep erythrocytes (SRBC) treated with 2-aminoethyl isothiouronium bromide. The purity of the resulting B lyphocyte preparation was checked with indirect immunofluorescent labelling with anti-(CD20) mAb B1 (Coulter Clone, Hialeah, FL) or anti-(CD3) mAb OKT3 (Ortho, Raritan, NJ) and a FITC-conjugated F(ab')$_2$ fragment of rabbit anti-(mouse Ig) (Zymed, San Francisco, Calif.), and FACS analysis. The B cell preparations contained (mean±SD of 6 isolations): 95±4% CD20-positive cells and 2±4% CD20-positive cells and 2±1% CD3-positive cells.

B-Cell Proliferation Assay

B cells (4×10$^4$ per well) were cultured in 200 μl IMDM supplemented with 10% fetal calf serum in flat bottom 96-well microtiter plates. B cells were stimulated by addition of immobilized anti-(IgM) antibodies (1mmunobeads; 5 μg/ml; BioRad, Richmond, Calif.). Where indicated, 100 U/ml recombinant IL-2 was added. Varying concentrations of mAbs were added at the onset of the microcultures and proliferation was assessed at day 3 by measurement of the incorporation of [$^3$H]-thymidine after eighteen hour pulsing.

Banchereau-Like-B-Cell Proliferation Assay

For testing the ability of anti-CD40 mAbs to stimulate B-cell proliferation in a culture system analogous to that described by Banchereau et al., *Science* (1991) 251:70, mouse 3T6 transfectant cells expressing the HR allelic form of human FcγRII were used. B cells (2×10$^4$ per well) were cultured in flat-bottom microwells in the presence of 1×10$^4$ transfectant cells (irradiated with 5000 Rad) in 200 μl IMDM supplemented with 10% fetal calf serum and 200 U/ml recombinant IL-4. Before addition of the B cells, the 3T6 cells were allowed to adhere to the culture plastic for at least five hours. Anti-CD40 mAbs were added at concentrations varying from 15 mg/ml to 2000 ng/ml and proliferation of B cells were assessed by measurement of thymidine incorporation at day 7, upon eighteen hour pulsing with [$^3$H]-thymidine.

B-Cell Activation Assay with EL4B5 Cells

B cells (1000 per well) were cultured together with irradiated (5000 Rad) EL4B5 cells (5×10$^4$ per well) in flat bottom microtiter plates in 200 μl IMDM supplemented with 10% heat-inactivated fetal calf serum, 5 ng/ml phorbol-12-myristate 13-acetate (Sigma) and 5% human T-cell supernatant. MAbs were added at varying concentrations at the onset of the cultures and thymidine incorporation was assessed at day 6 after 28 hour pulsing with [$^3$H]-thymidine. For the preparation of T-cell supernatant, purified T cells were cultured at a density of 10$^6$/ml for 36 hours in the presence of 1 μg/ml PHA and 10 ng/ml PMA. Wen et al. supra. T-cell supernatant was obtained by centrifugation of the cells and stored at −20° C. The effectiveness of T-cell supernatants in enhancing proliferation of human B cells in EL4B5-B cell cultures was tested and the most effective supernatants were pooled and used in the experiments.

Human T Cell Helper Assay for Antibody Production by Cells 96-well tissue culture plates were coated with a 1:500 dilution of ascites fluid of anti-CD3 mAb CLB-T3/3 (CLB, Amsterdam, The Netherlands). As indicated, costimulatory mAbs were added: anti CD2 mAbs CLB-T11.1/1 and CLB-T11.2/1 (CLB, Amsterdam, The Netherlands), both ascites 1:1000 and anti-CD28 mAb CLB-28/1 (CLB, Amsterdam, The Netherlands). Subsequently, tonsillar T cells (irradiated, 3000 Rad; 10$^5$ per well), tonsillar B cells (10$^4$ per well) and rIL-2 (20 U/ml) were added. The final volume of each cell culture was 200 μl. After eight days, cells were spun down, and cell-free supernatant was harvested. The concentrations of human IgM and IgG in (diluted) samples were estimated by ELISA as described below.

ELISA Assay for Immunoglobulin Quantification

The concentrations of human IgM and IgG were estimated by ELISA. 96-well ELISA plates were coated with 4 μ/ml mouse anti-human IgG mAb MH 16-01 (CLB, Amsterdam, The Netherlands) or with 1.2 μg/ml mouse anti-human IgM mAb 4102 (Tago, Burlingame, Calif.) in 0.05M carbonate buffer (pH =9.6), by incubation for 16 h at 4° C. Plates were washed three times with PBS-0.05% Tween-20 (PBS-Tween) and saturated with BSA for one hour. After two washes, the plates were incubated for one hour at 37° C. with different dilutions of the test samples. After three washes, bound Ig was detected by incubation for 1 hour at 37° C. with 1 μg/ml peroxidase-labeled mouse anti-human IgG mAb MH 16-01 (CLB) or mouse anti-human IgM mAb MH 15-01 (CLB). Plates were washed four times and bound peroxidase activity was revealed by the addition of o-phenylenediamine as a substrate. Human standard serum (H00, CLB) was used to establish a standard curve for each assay.

Flow Cytofluorometric Assay

ARC cells (10$^6$ cells/sample) were incubated in 100 μl primary antibody (10 μg/ml in PBS-BSA or Hanks' balanced salt solution (HBSS) supplemented with 1% BSA and 0.05% sodium azide) for twenty minutes at 4° C. After three washes with PBS-BSA or HBSS-BSA, the cells were incubated in 100 μl FITC-labeled F(ab')$_2$ fragments of goat anti-(mouse IgG) antibodies (Jackson, West Grove, Pa.) for twenty minutes at 4° C. After three washes with PBS-BSA or HBSS-BSA and one wash with PBS, the cells were resuspended in 0.5 ml PBS. Analyses were performed with a FACSCAN V (Becton-Dickinson, San Jose, Calif.).

Alternatively, EL4B5 cells were harvested before and at different time points during culture in medium containing PMA (5 ng/ml) and human T-cell supernatant (5%). Cells were incubated for thirty minutes with 10 Itl supernatant of transfected cells containing hCD40.hμ diluted in 100 μl Hank's Balanced Salt Solution supplemented with 0.05% sodium azide (4° C). This was followed by incubation with FITC-conjugated F(ab')$_2$ fragments of rabbit anti-(human IgM) (Central Laboratory of the Netherlands, Blood Transfusion Service, Amsterdam, The Netherlands). As a control, cells were incubated with the FITC-conjugate only. For analysis, a FACScan-4 cytofluorometer (Becton-Dickinson) was used. Non-vital cells were excluded from analysis by the use of propidium iodide.

c) Humanized Monoclonal Antibodies

The monoclonal antibodies of the present invention, which are capable of blocking the CD40-CD40 ligand interaction, are a useful therapeutic tool in treating autoimmune diseases. However, because many of the monoclonal antibodies of the present invention are directed from a non-human (e.g., murine) cell line, the antibodies may be recognized over time as foreign by the human recipient and an immune response may be mounted which would neutralize subsequent administrations of the monoclonal antibodies. Because the immunogenicity of a foreign protein is largely determined by the nature of the surface, it was decided that the immunogenicity of any monoclonal antibodies of the present invention that were derived from non-human cell lines could be reduced or abolished if an effective number of the exposed (i.e., surface) amino acids in the framework regions of the antibody were replaced with those amino acids usually found in human antibodies.

Techniques for humanizing monoclonal antibodies are well known in the art. Moreover, the techniques for humanizing a monoclonal antibody which are disclosed in the following publications, are expressly incorporated herein by reference:

1) Rodwell, "Engineering Monoclonal Antibodies," Nature, 342:99–100 (1989);
2) Reichmann, et al., "Reshaping Human Antibodies For Therapy," Nature, 332:323–327 (1988);
3) Waldman, Thomas, "Monoclonal Antibodies in Diagnosis and Therapy," Science, 252:1657–1662 (1991);
4) Oi, et aL, "Chimeric Antibodies," BioTechniques, 4(3):214:221 (1986);
5) Liu, et al. "Production Of A Mouse-Human Chimeric Monoclonal Antibody To CD20 With Patent Fc-Dependent Biologic Activity," J. Immunol., 139:3521–3526 (1987);
6) Beidler, et al., "Cloning and High Level Expression of A Chimeric Antibody With Specificity For Human Carcinoembryonic Antigen," J. Immunol., 141:4053–4060 (1986);
7) Jones, et al., "Replacing The Complementarity-Determining Regions In A Human Antibody With Those From A Mouse," Nature, 321:522–525 (1986);
8) Wood, et aL, "The Synthesis And In Vivo Assembly of Functional Antibodies In Yeast," Nature, 314:446–449 (1985);
9) U.S. Pat. No. 4,816,567 (Cabilly, et al.) "Recombinant Immunoglobulin Preparations";
10) Morrison, "Transfectomas Provide Novel Chimeric Antibodies," Science 229:1202–1207 (1985);
11) Better, et al., "Escherichia coli Secretion of an Active Chimeric Antibody Fragment," Science, 240:1041–1043 (1988);
12) Boulianne, G. L., et al., "Production of Functional Chimaeric Mouse/Human Antibody," Nature 312:643–646 (1984); and
13) Heuberger, et al., "A Hapten-specific Chimaeric IgE antibody With Human Physiological Effector Function," Nature 314: 268–270 (March, 1985).

For example, to humanize a monoclonal antibody, the variable heavy (VH) chain and the variable light (VL) chain of the monoclonal antibody to be humanized are cloned, sequenced, compared to a series of the most homologous human sequences and then the DNA sequence encoding the monoclonal antibody is modified by site directed mutagenesis. In particular, messenger RNA encoding the monoclonal antibody to be humanized is obtained from the hybridoma producing that antibody. To obtain mRNA encoding the monoclonal antibody, the hybridoma cells are washed twice with phosphate buffered saline and lysed with quanidium thiocyanate in the presence of 0.7M 2-mercaptoethanol. The cell lysate is layered on a discontinuous CsCl gradient and centrifuged for about sixteen hours at 26,000 rpm in a Beckman centrifuge having an SW28 rotor. The RNA is recovered by dissolving the resulting pellet in diethyl pyrocarbonate-treated $H_2O$ (DEPC-treated $H_2O$). The RNA is precipitated with ethanol once resuspended in DEPC-treated $H_2O$, and stored at $-70°$ C.

Amplification of the cDNA encoding the heavy and light chain variable regions of the mAb is accomplished by polymerase chain reaction (PCR) using a set of degenerate primers with restriction sites for cloning. The typical primer set consists of eight 5' primers for the variable region of the heavy chain (VH) that are combined with one universal 3' primer located in the constant region of the heavy chain (CH), and five 5' primers for the variable region of the light chain (VL) that are combined with one universal 3' primer located in the constant region of the light chain (CL). Optionally, a determination is made that one of the primer sets is best suited for the amplification of the VH and VL regions. Thereafter, multiple PCR runs are performed using a low cycle number to avoid incorporation of PCR mistakes. The PCR products obtained after about 24 amplification cycles are subcloned in the polylinker of a sequencing vector. Several (e.g., six) independent clones are analyzed for both VH and VL. This results in a consensus sequence for the cDNA and the deduced protein sequence of the VH and VL regions, respectively of the monoclonal antibody. The deduced protein sequence is overlayed with the location of the framework regions (FR) and the complementarity determining regions (CDR) which form the antigen-binding site of the antibody.

To produce a humanized antibody with the least likelihood of generating an immune response in a human, the deduced protein sequences of the VH and VL regions are used to search different data bases for human antibody sequence with the best homology to the monoclonal antibody (or fragment if only a fragment is to be humanized.) The results are tabulated for the VH and VL regions. Several (e.g., three) of the best matching human antibody sequences are used to determine which of the non-human amino acids in the exposed framework should be changed to a human amino acid in order to obtain a humanized version of the monoclonal antibody.

PCR primers are designed to change the selected exposed residues from non-human to human. Those skilled in the art recognize that the encoding number of mutagenic primers that are designed depends upon the number of mutagenic sites to be introduced into the VH and VL regions. For example, to introduce a total of seven non-adjacent mutagenic sites in both the VH and VL regions, a total of eight primers are designed for the mutagenesis of the VH region, and likewise eight primers are designed for the VL region. cDNA encoding the non-human sequence is used as template for the PCR reactions. Both the humanized variable heavy region ($VH_x$) and the humanized variable light region ($VL_x$) region are constructed in three consecutive PCR steps. After the final PCR step, the PCR construct is subcloned in the polylinker of a sequencing vector.

The $VH_x$ and $VL_x$ subclones are transferred using standard techniques from the sequence vectors to expression vectors that already coded part of the human constant heavy ($CH_H$) region and the complete human constant light ($CL_H$) region, thereby producing an expression vectors encoding VHXCHH and $VL_xCL_H$, respectively. The expression vectors coding $VH_xCH_H$ and $VL_xCL_H$ are cotransfected into Sf9 insect cells, whereupon the transfected insect cells secrete the antibody as a humanized monoclonal antibody fragment.

Alternatively, to prepare a chimeric monoclonal antibody from a non-human monoclonal antibody, the variable regions of the original non-human (e.g., mouse) heavy and light chains ($VH_M$ and $VL_M$) of the monoclonal antibody, as described above were transferred respectively into the expression above that already coded the $CH_H$ and $CL_H$ regions of a human Fab fragment, thereby producing expression vectors encoding $VH_M CH_H$ and $VL_M CL_H$ into Sf9 insect cells, the transfected insect cells secrete the antibody as a human/mouse chimeric monoclonal antibody fragment.

Example 1

Making Monoclonal Antibodies to B7 and CD40

A. PCR Cloning of CD40 and B7

RNA was isolated from a population of EBV-transformed human spleen cells, essentially as described by Chirgwin et al., *Biochemistry* (1979) 17:5294. In brief, the cells were washed twice with phosphate buffered sale (PBS) and lysed in 5M guanidinium thiocyanate in the presence of 0.7M 2-mercaptoethanol. The cell lysate was layered on a discontinuous CsCl gradient (Chirgwin et al.) and centrifuged for sixteen hours at 26,000 rpm in a Beckman SW28 rotor. The RNA was recovered by dissolving the pellet in DEPC-treated $H_2O$. The RNA was precipitated with ethanol once, resuspended in DEPC-treated $H_2O$, and stored at –70° C.

Total RNA (10 μg/reaction) was converted to cDNA using random hexamer priming in 50 μl reaction buffer containing 500 units MLV-RT (Bethesda Research Laboratories, Bethesda, Md.), 5 μM random hexamer (Pharmacia, Piscataway, N.J.), 1 mM $MgCl_2$ and 0.1 mg/ml BSA (bovine serum albumin). After incubation at 37° C. for one hour, the samples were boiled for three minutes and stored at –70° C. The DNA encoding the CD40 and B7 molecules was generated by PCR using primers which contained sequences having homology to known CD40 and B7 sequence, where the primers also encoded restriction sites useful for cloning (FIG. 2). These primers were based on the published cDNA coding sequences for B7 and CD40. Freeman et al., *J. Immunol.* (1989) 143:1714, and Stamenkovic et al., *EMBO J.* (1989) 8:1403. All primers start with a C-G clamp at the 5' end followed by a restriction site for cloning (shown in bold, FIG. 2). The underlined sequences in the backward primers, for the cloning of the soluble forms of B7 and CD40, represents an epitope recognized by a monoclonal antibody used for affinity purification. The numbers in brackets represent the location of the primers relative to the published cDNAs for CD40 and B7.

For PCR amplification, 1 μl of cDNA was mixed with 1 μl (10 picomoles) of a forward primer, 1 μl (10 picomoles) of a backward primer, and 47 μl of PCR mix. The PCR mix consisted of 1.25 units Taq polymerase (Perkin-Elmer/Cetus, Norwalk, Conn.), DNTP mix (0.2 mM each), 10 mM tris-HCl pH 8.3, 50 mM KCl, 2.5 mM $MgCl_2$ and 0.1 mg/ml BSA. The 50 μl of PCR mixture was overlaid with 70 μl mineral oil and subjected to 25 cycles of amplification in a Perkin-Elmer/Cetus thermocycler (denaturation at 95° C. for thirty seconds, primer annealing at 55° C. for thirty seconds and extension at 72° C. for 1.5 minutes). PCR products were obtained after 25 amplification cycles.

Figure 1B:
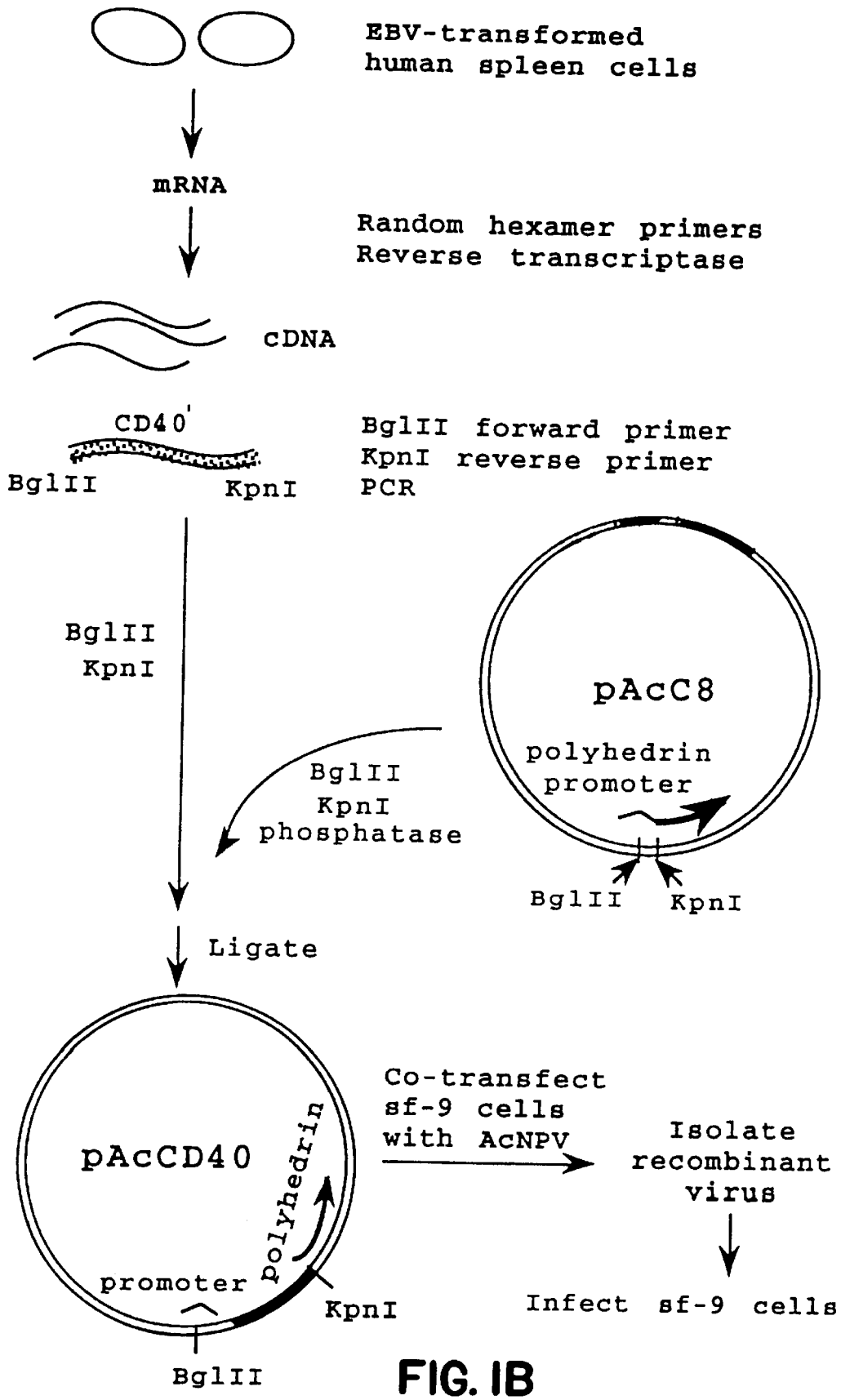
FIG. 1B shows a schematic representation of the generation of Sf9 cells which express human CD40 or B7 antigen.

The amplification products were digested with BglII and KpnI (FIG. 1B) and isolated by size-fractionation. Before expression in baculovirus, the DNA sequence of each fragment was confirmed by sequencing analysis to prevent the introduction of PCT-induced mutations. The baculovirus transfer vector pAcC8 was also digested with BglII and KpnI (FIG. 1B).

The amplified fragments were ligated to the linear pAcC8 vector (ratio of insert to vector was 3:1). The ligation products were transformed into bacterial strain DH5α (Gibco/BRL, Gaithersburg Md.) and recombinant pAcC8 vectors were selected on the basis of ampicillin resistance. Recombinant plasmids were isolated from bacterial clones (Maniatis et al., *Molecular Cloning: A Laboratory Manual*, (Cold Spring Harbor, N.Y.: Cold Spring Harbor Laboratories, 1982; Ausubel et al., *Current Protocols in Molecular Biology* (Media, Pa.: John Wiley and Sons)) and the presence of the insert of interest verified using polymerase chain reactions (see above). Large scale plasmid preparation was performed by standard procedures (Ausubel et al.; Maniatis et al., Sambrook et al., *Molecular Cloning: A Laboratory Manual*, (Cold Spring Harbor, N.Y.: Cold Spring Harbor Laboratories), 1989).

B. Baculovirus Expression of Human CD40 and B7

Sequences encoding human CD40 and human B7 were recombined into the Autographa californica baculovirus (AcNPV) using the transfer vectors pAcCD40 (encoding the full-length CD40 molecule), pAcCD40-ED/Glu (encoding the extracellular domain of CD40), pAcB7 (encoding the full-length B7 molecule) and pCcB7-ED/Glu (encoding the cellular domain of the B7 molecule).

The plasmids were cotransfected with wild-type baculoviral DNA (2–10 pfu) (AcNPV; Summers et al., *A Manual of Methods for Baculovirus Vectors and Insect Cell Culture Procedures*, Texas Agricultural Experimental Station Bulletin No. 1555 (1987) into Sf9 (*Spodoptera frugiperda*) cells at a density of $10^6$ cells/ml (Summers et al.). Recombinant baculovirus-infected Sf9 cells were identified and clonally purified (Summers et al.).

For cell surface expression of recombinant proteins, the cells were harvested after forty-eights hours of culture.

C. Sf9 Insect Cell ELISA

Sf9 insect cells infected with recombinant virus were cultured for 48 hours in 24-well plates. After removal of the tissue culture medium, the plates were incubated for 45 minutes at room temperature (RT) with 0.25 ml of antibody in PBS with 1% BSA (PBS-BSA). After three washes with PBS-BSA, the plates were incubated for 35 minutes at RT with 250 μl of a 1/250 dilution of goat anti-(mouse total Ig) immunoglobulins conjugated to horseradish peroxidase (Zymed, South San Francisco, Calif.) in PBS-BSA. Unbound peroxidase activity was removed by washing five times with PBS-BSA. Bound peroxidase activity was revealed by the addition of an assay mixture prepared by diluting 0.5 ml of 2 mg/ml 3,3',5,5'-tetramethylbenzidine in ethanol to 10 ml with 10 mM sodium acetate, 10 mM EDTA buffer (pH 5.0) and adding 0.03% (v/v) $H_2O_2$. The reaction was stopped after ten minutes by adding 100 μl of 1M $H_2SO_4$.

Figure 3:
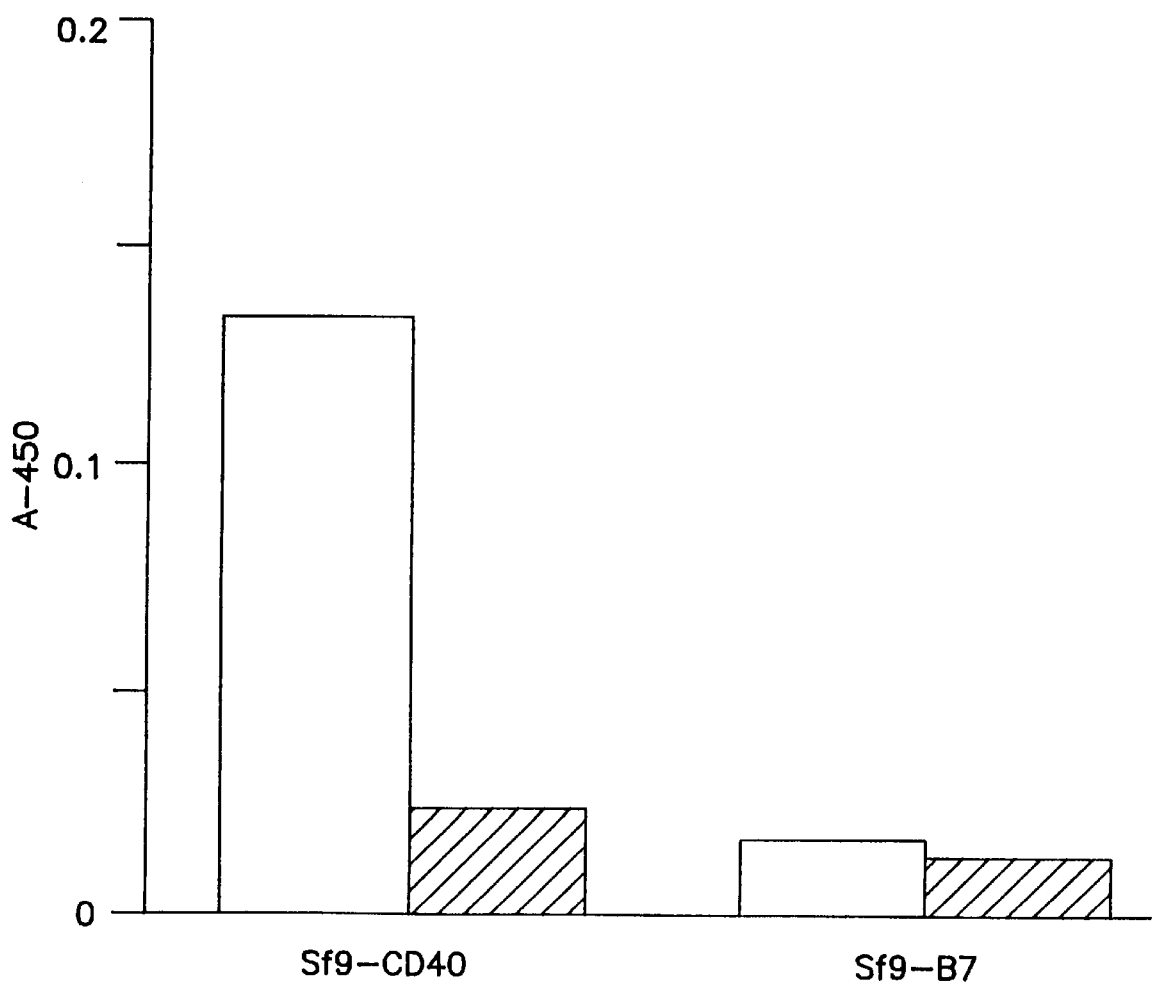
FIG. 3 shows the results of ELISA assays examining the reaction of anti-CD40 monoclonal antibody S2C6 with Sf9 cells expressing CD40 and with Sf9 cells expressing B7.

The above-described EUISA assays performed on live Sf9 cells gave the following results. FIG. 3 presents the data for life Sf9 cells infected with pAcB7 and pAcCD40 which were cultured for 48 hours in 24-well plates. The antibodies used in the EUISA to generate FIG. 3 were: S2C6 (anti-CD40, open bars) and no primary antibody (hatched bars).

D. Host Animal Immunization

Female BALB/c mice were injected intraperitoneally at day 0 and day 14 with $5\times10^6$ Sf9 cells infected with AcCD40 virus, AcB7 virus or AcCD3 virus (control virus). At day 21, 100 μl of serum was obtained to test for the presence of specific antibodies. After a rest period of at least two weeks, the mice received a final injection with $5\times10^6$ cells infected with AcCD40 or AcB7 virus. Three days after this last injection, the spleen cells were used for cell fusion.

E. Generation of Hybridoma Clones

Splenocytes from immunized BALB/c mice were fused with SP2/0 murine myeloma cells at a ratio of 10:1 using 50% polyethylene glycol as previously described by de Boer et al., *J. Immunol.* Meth. (1988)113:143. The fused cells were resuspended in complete IMDM medium supplemented with hypoxanthine (0.1 mM), thymidine (0.016 mM) and 0.5 ng/ml hIL-6 (Genzyme, Cambridge, Mass.). The fused cells were then distributed between the wells of 96-well tissue culture plates, so that each well contained 1 growing hybridoma on average.

Figure 4C:
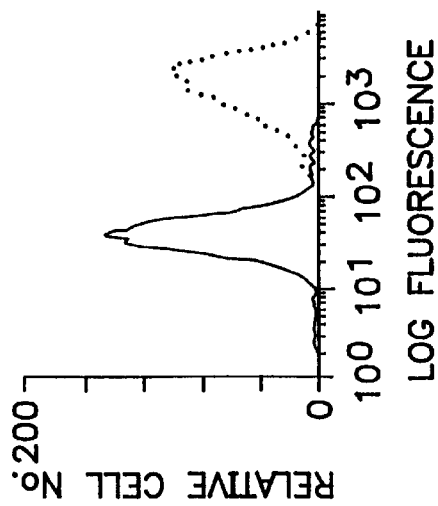
FIG. 4 shows the results of the fluorescent cell staining of EBV-transformed B-cell line ARC cells expressing CD40.
Figure 4B:
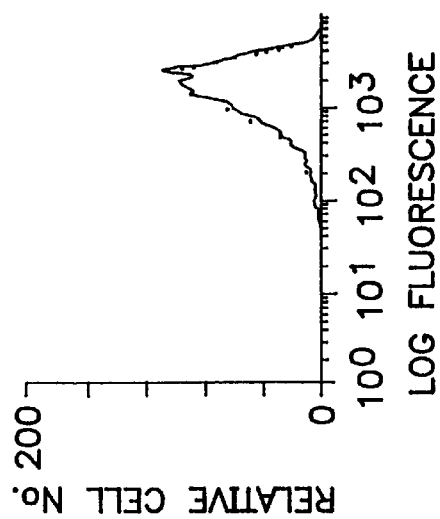
Figure 4A:
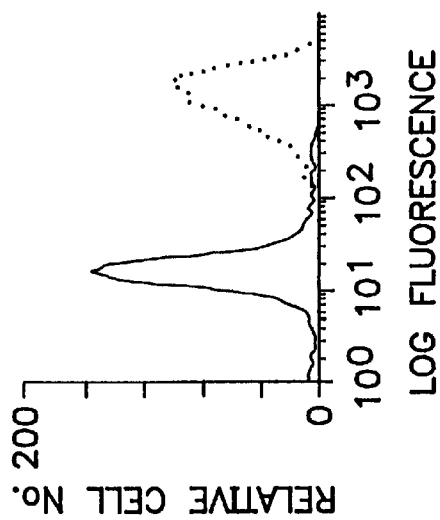

After 10–14 days, the supernatants of the hybridoma populations were screened for specific antibody production. For the screening of specific antibody production by the hybridoma clones, the supernatants of twelve wells were pooled and used for fluorescent cell staining of EBV-transformed B cells as described for the FACS Assay above. Subsequently, the supernatants of the positive pools were tested individually. Positive hybridoma cells were cloned three times by limiting dilution in IMDM/FBS containing 0.5 ng/ml hIL-6. Three hybridomas producing anti-CD40 antibodies are labelled 5D12, 3A8 and 3C6. The data is presented in FIG. 4, which shows that a soluble form of CD40, but not of B7 can block the binding of the anti-CD40 mAb 5D12 to CD40 expressing EBV-transformed B cells. FIG. 4 shows fluorescent cell staining of ARC EBV-transformed B cells with 5D12 is the presence and absence of soluble B7 and soluble CD40. 5D12 and the soluble B7, soluble CD40, or controls were preincubated at RT for 20 minutes before addition to the ARC cells. FIG. 4A shows staining with 5D12 (dotted line) or second antibody only (solid line). FIG. 4B shows staining with 5D12 alone (dotted line) or preincubated with soluble B7 (solid line). FIG. 4C shows staining with 5D12 alone (dotted line) or preincubated with soluble CD40.

Example 2

Costimulation of B-Cell Proliferation Using Anti-CD40 mAbs

Four hybridomas producing monoclonal antibodies against human CD40 were generated in Example 1. These mAbs were shown to bind to a similar proportion of tonsillar B cells as anti-CD40 mAb G28.5 does. de Boer et al. *J. Immunol. Methods* (1992) 152:15. Three of these monoclonal antibodies (5D12, 3A8 and 3C6) which were of the IgG2b subclass, were tested for their ability to deliver activation signals to human B cells in the B-cell proliferation assay described above.

Figure 5A:
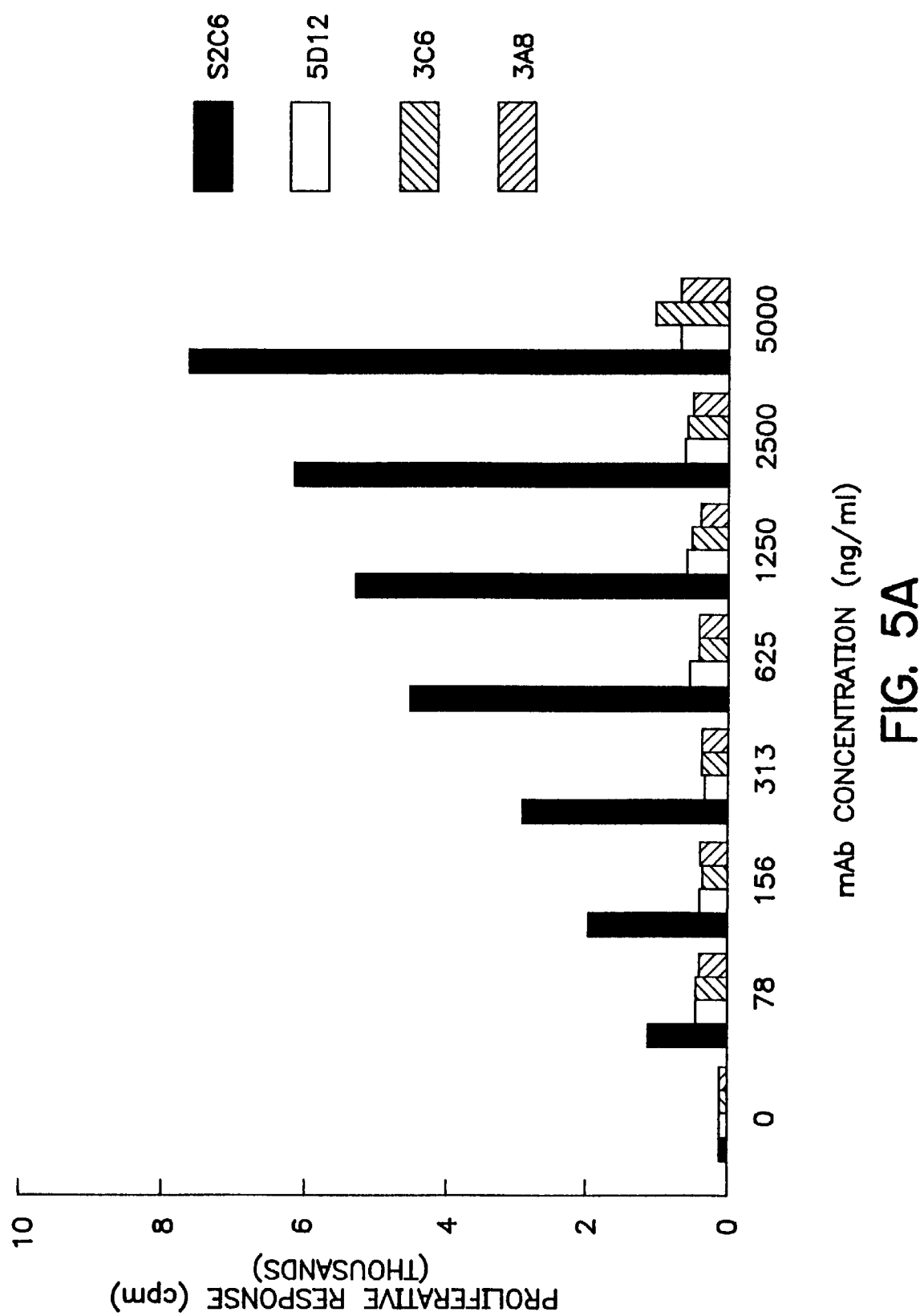
FIG. 5A compares the ability of three new (5D12, 3C6 and 3A8) and one old (S2C6) anti-CD40 mAbs to co-stimulate anti-IgM induced human B-cell proliferation.
Figure 5B:
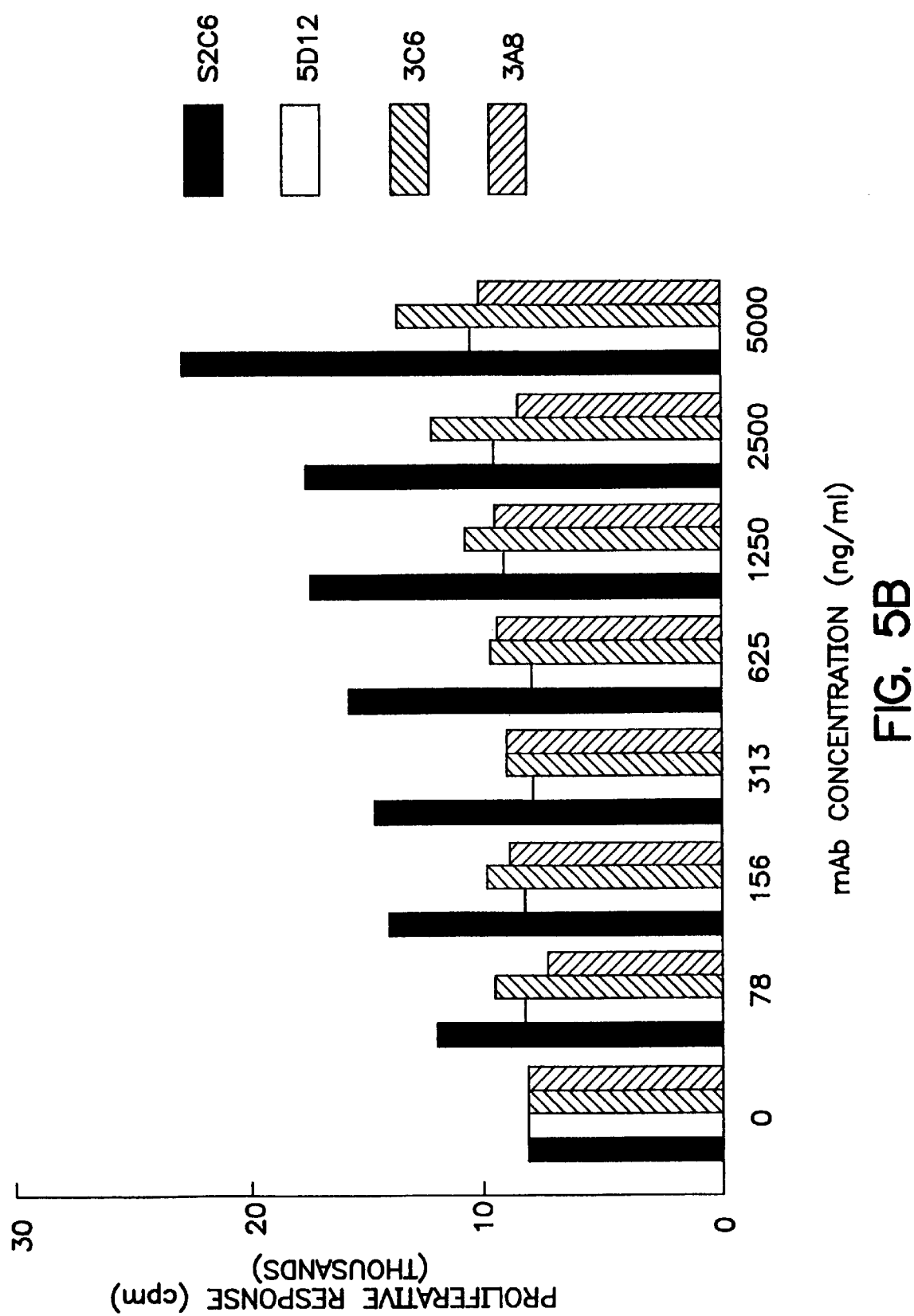
FIG. 5B repeats the experiment of FIG. 5A in the presence of recombinant interleukin-2 (rIL-2).

Human tonsillar B cells ($4 \times 10^4$ per well) were cultured in 200 µl in microwells in the presence of anti-IgM coupled to Sepharose beads (5 µ/ml) (FIG. 5A) or in the presence of anti-IgM plus rIL-2 (100 U/ml) (FIG. 5B). Varying concentrations of the anti-CD40 mAbs S2C6, 5D12, 3C6 or 3A8 were added and [$^3$h]thymidine incorporation was measured at day 3 after 18 hours of pulsing. Data presented in FIG. 5A are means derived from experiments with B-cell preparations from three different donors with duplicate incubations. Data of FIG. 5B are means of duplicate incubations from one experiment out of two with comparable results.

None of the novel anti-CD40 mAbs was able to significantly costimulate human B-cell proliferation in the presence of immobilized anti-IgM or in the presence of immobilized anti-IgM and IL-2. In contrast, anti-CD40 mAb S2C6 costimulated human B-cell proliferation in a concentration dependent fashion.

Example 3

Induction of B-Cell Proliferation Using Anti-CD40 mAbs

The mAbs tested in Example 2 were tested for their ability to induce proliferation of human B cells in the Banchereau-like Assay described above, i.e., by presenting the anti-CD40 mAb on adherent cells expressing FcγRII. As antibody presenting cells, mouse 3T6 transfectant cells expressing the HR allelic form of human FcγRII were used. It was observed that anti-CD40 mAb S2C6 together with IL-4 induced substantial proliferation of tonsillar human B cells in this system, as assessed by measurement of [$^3$H] thymidine incorporation. Anti-CD50 mAbs 5D12, 3C6 or 3A8, however, did not induce proliferation of human B cells in this culture system (data not shown).

Example 4

Inhibition of S2C6 Stimulated B-Cell Proliferation Using Anti-CD40 mAbs

The mAbs were also tested for their ability to inhibit the costimulation of human B-cell proliferation by anti-CD40 mAb S2C6 using the B-cell proliferation Assay described above. Human tonsillar B cells ($4 \times 10^4$ per well) were cultured in 200 µl in microwells in the presence of anti-IgM coupled to Sepharose beads (5 µg/ml) and anti-CD40 mAb S2C6 (1.25 µg/ml). Varying concentrations of anti-CD40 mAbs 5D12, 3C6 or 3A8 were added and [$^3$H]thymidine incorporation was assessed after three days. As a control anti-(glucocerebrosidase) mAb 8E4 was added in similar concentrations. Barneveled et al. *Eur. J. Biochem.* (1983) 134:585. Data are means ±S.D. derived from experiments with B cells from two different donors with duplicate incubations.

Figure 6:
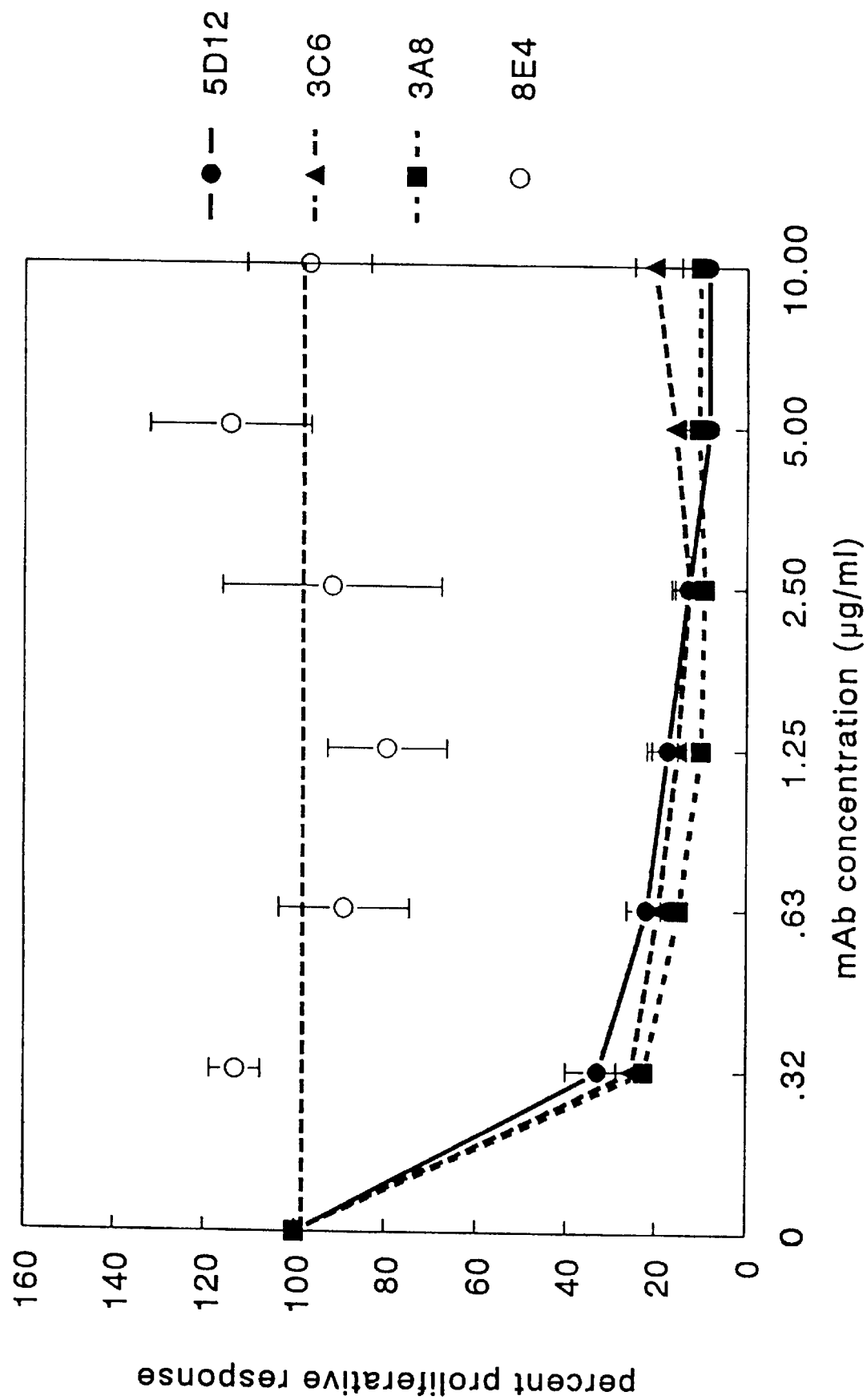
FIG. 6 shows the ability of three new anti-CD40 mAbs to inhibit human B-cell proliferation induced by costimulation with immobilized anti-IgM and anti-CD40 mAb S2C6.

It was found that each of the anti-CD40 mAbs 5D12, 3A8 and 3C6 could inhibit the costimulation of anti-IgM induced human B-cell proliferation by mAb S2C6 (FIG. 6). In contrast, no significant inhibition was seen with equivalent amounts of non-relevant mAb 8E4, directed to β-glucocerebrosidase. Barneveld et al., supra. Thus, it as concluded that these anti-CD40 mAbs do not deliver stimulatory signals to cause the proliferation of human B cells, but, conversely, can inhibit stimulatory signals exerted by triggering CD40 with another mAb. Therefore, these mAbs were considered to be excellent tools to investigate whether signaling via CD40 plays a role in the stimulation of human B-cell proliferation by EL4B5 cells.

Example 5

Effects of Anti-CD40 mAbs on EL4B5-Induced Human B-Cell Proliferation

The effects of anti-CD40 mAbs on EL4B50-induced human B-cell proliferation was tested using the B-cell Activation Assay described above. Human tonsillar B cells (1000 per well) were cultured together with irradiated EL4B5 cells (50,000 per well) in the presence of 5% supernatant of activated human T cells and 5 ng/ml PMA. Anti-CD40 mAbs 5D12, 3C6 or 3A8 were added in varying concentrations. As a control, mAb MOPC-141 (IgG2b) was added. After six days of culture, [$^3$H]thymidine incorporation was assessed.

Figure 7:
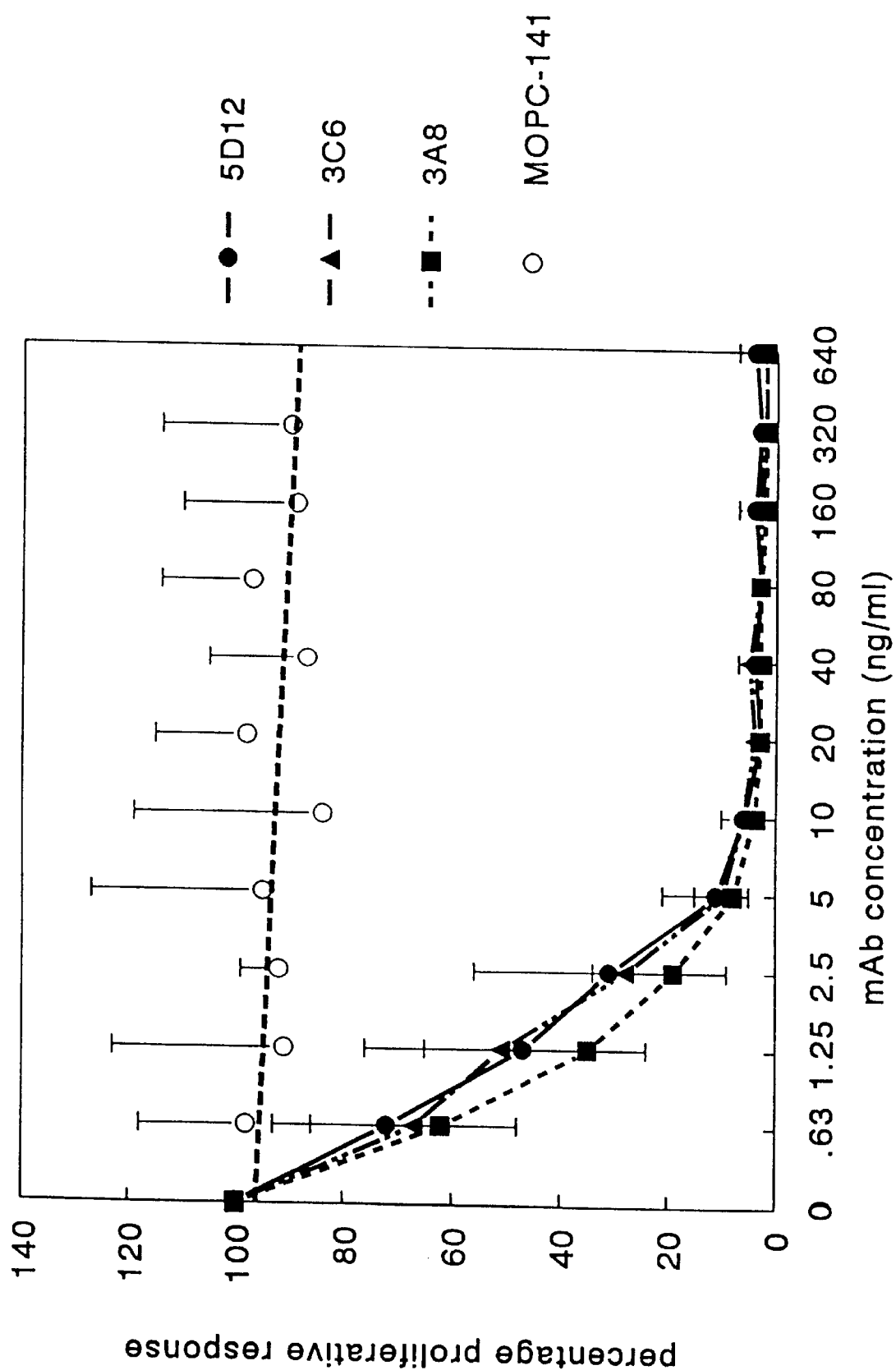
FIG. 7 shows the effect of three new anti-CD40 mAbs on EL4B5-induced human B-cell proliferation.

FIG. 7 shows that addition of anti-CD40 mAbs 5D12, 3C6 or 3A8 resulted in a concentration-dependent inhibition of human B-cell proliferation. Data are means±S.D. derived from experiments with B cells from four different donors with duplicate incubations. [$^3$H]-thymidine incorporation values found for incubations without mAb were (means±S.D.) 10460±1843 cpm, 6982±1729 cpm, 4362±1020 cpm and 1543±3190 in the four different experiments, respectively. [$^3$H]-thymidine incorporation in B cells alone amounted to 40±5 cpm and in irradiated EL4B5 cells alone 31±15 cpm.

Very potent inhibition occurred. At concentrations as low as 10 ng/ml each, the three anti-CD40 mAbs 5D12, 3C6 and 3A8 inhibited human B-cell proliferation completely. Half-maximal inhibition was found at about 1 ng/ml. In contrast, isotype matched IgG2b mouse myeloma protein MOPC-141 had no significant effect on [$^3$H]-thymidine incorporation. Similarly inhibition was observed when [$^3$H]-thymidine incorporation was assessed at day 4 of the culture instead of day 6, thus excluding the possibility that the observed effect was due to a change in the kinetics of the proliferation under influence of the anti-CD40 mAb (data not shown).

For comparison, the influence of a few mAb directed against other B-cell surface structures was investigated. Neither anti-CD20 mAb B1 or anti-B7 mAb B7-24 (the latter mAb was generated by a procedure similar to that used for generating the anti-CD40 mAb used in FIG. 7) in concentrations similar to those used in the experiments with the anti-CD40 mAb, had any effect on EL4B5-induced human B-cell proliferation (data not shown). Therefore, it may be concluded that the inhibitory effect of anti-CD40 mAb on EL4B5-induced B-cell proliferation is not due to masking of the B-cell surface.

Example 6

Effects of hCD40.hμ on EL4B5-Induced Human B-Cell Proliferation

Figure 8:
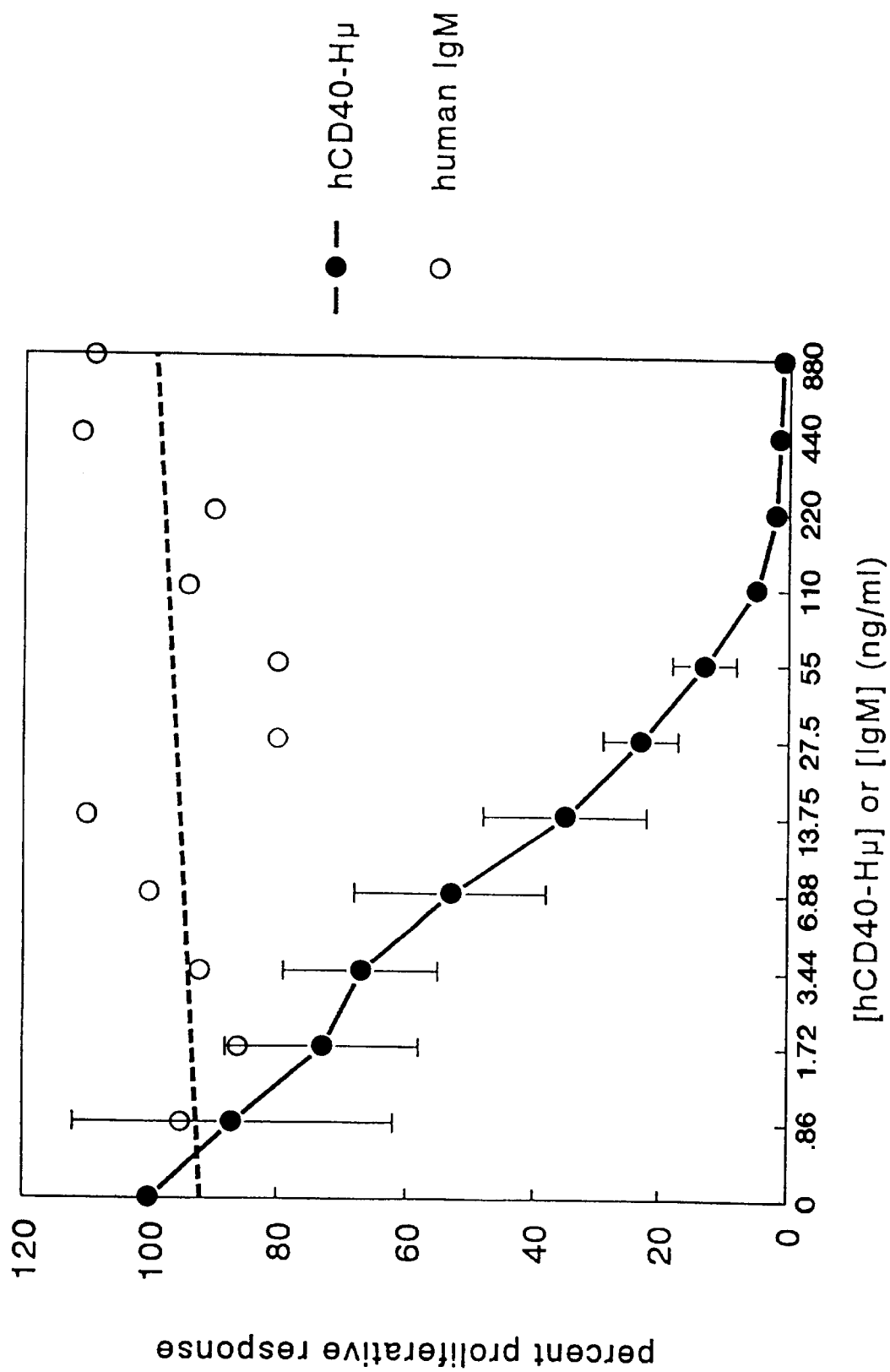
FIG. 8 shows the effect of soluble CD40 (hCD40.hμ) on EL4B5-induced human B-cell proliferation.

In order to investigate whether EL4B5 cells expressed a membrane structure which binds CD40, a fusion protein consisting of the extracellular domain of CD40 and human IgM constant domains $CH_2$, $CH_3$ and $CH_4$ (hCD40.hμ) was used for flow fluorocytometric analysis. Lane et al., supra. Non-activated EL4B5 cells did not bind the fusion protein. However, upon culturing EL4B5 cells together with PMA (5 ng/ml) and 5% human T-cell supernatant, which are the conditions needed for activation of human B cells, a low binding of hCD40.hμ was found (data not shown). This small shift in fluorescence was found consistently in three independent experiments. The minimal activation period needed for induction of the CD40 binding was 24 hours. To determine whether binding of hCD40.hμ to the EL4B5 cells would inhibit EL4B5-induced human B-cell proliferation like anti-CD40 mAb did, the fusion protein was titrated into cocultures of EL4B5 cells with human B cells using the B-cell Activation Assay described above. FIG. 8 shows that the fusion protein did indeed inhibit [$^3$H]-thymidine incorporation in a concentration-dependent manner and, like the anti-CD40 mAb used in the experiments shown in FIG. 7, was able to inhibit B-cell proliferation induced by the EL4B5 cells completely.

Example 7

Figure 9A:
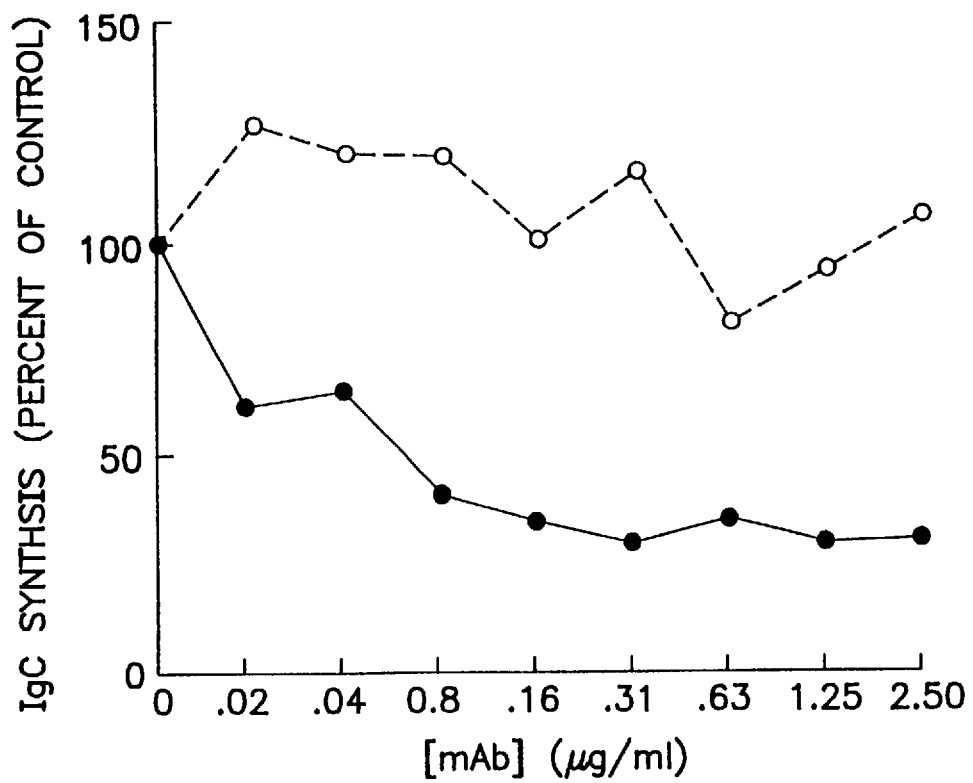
FIGS. 9A and 9B show the effect of one new anti-CD40 mAb 5D12 on human T-cell induced immunoglobulin production of human B cells.

Effects of Anti-CD40 mAbs on Human T-Cell-Induced Antibody Production by Human B-Cells The antibodies were also tested for their capacity to inhibit immunoglobulin production by B cells, stimulated in a contact-dependent manner with activated T cells using the T-cell helper assay described above. Human tonsillar B cells ($10^4$/well) were cultured together with irradiated purified T cells (3000 rad, $10^5$/well) in 96-well plates, coated with anti-CD3 mAb and with or without different mAbs to costimulate the T cells. After 8 days of culture the supernatants were harvested for the determination of immunoglobulin production by the B cells. Immunoglobulin production by the B cells was assessed by the ELISA assay described above. Anti-CD40 mAb 5D12 was added in varying concentrations from the onset of the cultures. As a control, mAb 5D12 was added in varying concentrations from the onset of the cultures. As a control, mAb MOPC-141 was added. FIG. 9A shows that when T cells were stimulated with immobilized anti-CD3 mAb and costimulated with soluble anti-CD2 and anti-CD28 mAbs, addition of anti-CD40 mAb 5D12 resulted in a concentration dependent inhibition of IgG production by human B cells. IgM production by the B cells was inhibited to the same extent. Similar results were obtained with the anti-CD40 mAbs 3C6 and 3A8 and with the hCD40.hμ fusion protein.

The anti-CD40 mAbs of this invention exhibited very potent inhibity. At concentrations as low as approximately 30 ng/ml, each of the three anti-CD40 mAbs gave a 50% of maximal inhibition. In contrast, the isotype-matched $IgG_{2b}$ mouse myeloma protein MOPC-141 had no effect on the immunoglobulin production.

Figure 9B:
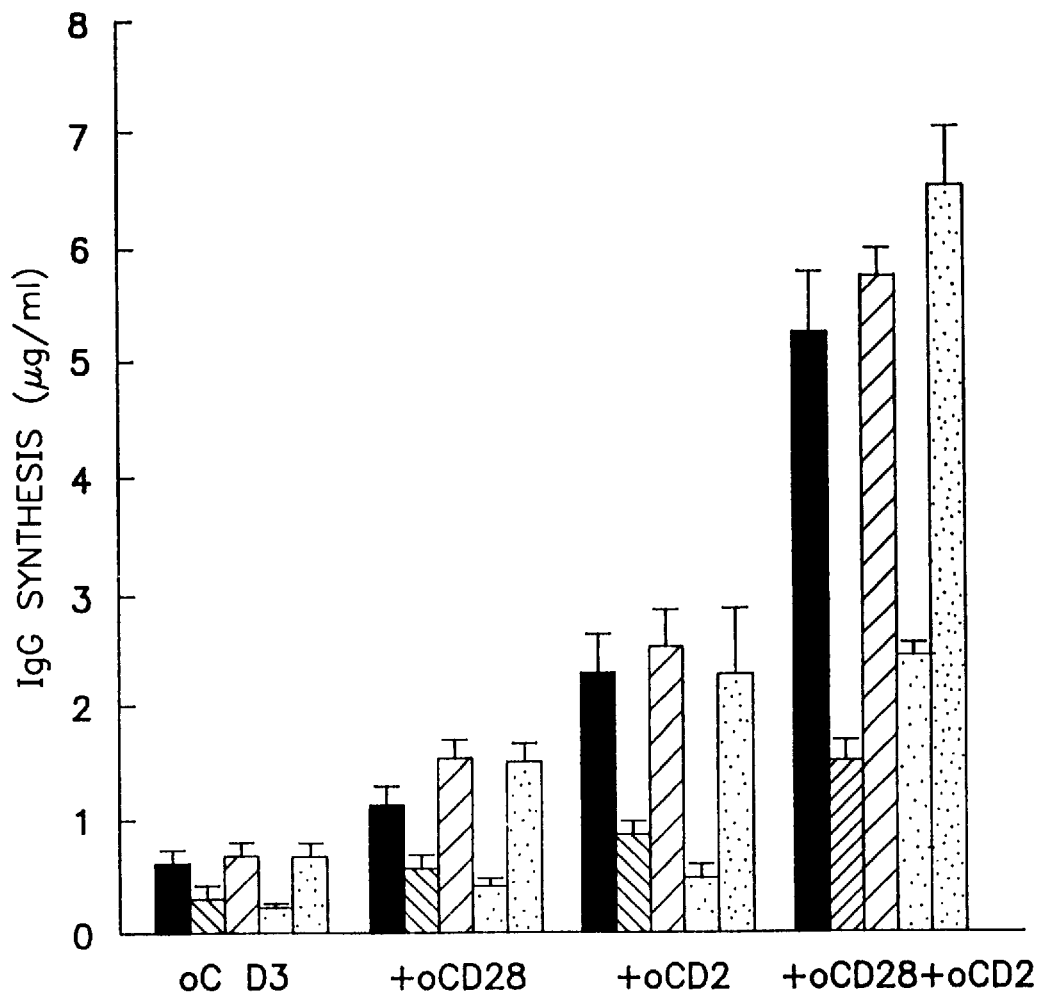

The inhibitory effect by the three anti-CD40 mAbs was not specific for the manner of activation of the T cells providing the CD40 ligand helper activity. FIG. 9B shows that under all the T-cell stimulation conditions (anti-CD3 alone; anti-CD3+anti-CD2; anti-CD3+anti-CD28; and anti-CD3+anti-CD 2+anti-CD28), the addition of the anti-CD40 mAb 5D12 results in strong inhibition of immunoglobulin production by the human B cells. The inhibition is comparable to the amount of inhibition with the hCD40.hμ fusion protein, known to completely block the CD40-CD40 ligand interaction. The percentage of inhibition varied from 40 to 70% depending on the T-cell activation conditions. In contrast, the isotype-matched $IgG_{2b}$ mouse myeloma protein MOPC-141, or human IgM (as control for the hCD40.hμ fusion protein) had no effect on immunoglobulin production by the human B cells.

Example 8

Humanizing Anti-CD40 Monoclonal Antibodies

Any of the anti-CD40 monoclonal antibodies of the present invention are capable of being humanized using any of the techniques expressly incorporated herein by reference supra or the following techniques as applied to monoclonal antibody 5D12.

To humanize the Fab fragment of the 5D12 monoclonal antibody, the variable heavy (VH) chain and the variable light (VL) chain of 5D12 monoclonal antibody were first cloned and then sequenced. To obtain messenger RNA encoding for the 5D12 monoclonal antibody, the hybridoma cells that produce the 5D12 monoclonal antibody were washed with phosphate buffered saline, lysed in 5M guanidinum thiocyanate in the presence of 2-mercaptoethanol (see Example 1A). The lysate was then incubated with oligo-dT beads to bind the mRNA. To amplify the variable (VH and VL) regions of 5D12, the mRNA was used in RT-PCR employing degenerate primers for the IgG variable light (VL) chain or variable heavy (VH) chain. RT-PCR is a modification of the PCR technique that permits the amplification of sequences found in RNA target polynucleotides by first generating a cDNA product which is then amplified by PCR. The RT-PCR technique is well known in the art and is incorporated herein by reference to Myers et al., Biochemistry 30:7661–7666 (1991) and U.S. Pat. Nos. 5,310,652 and 5,407,800.

Figure 10:
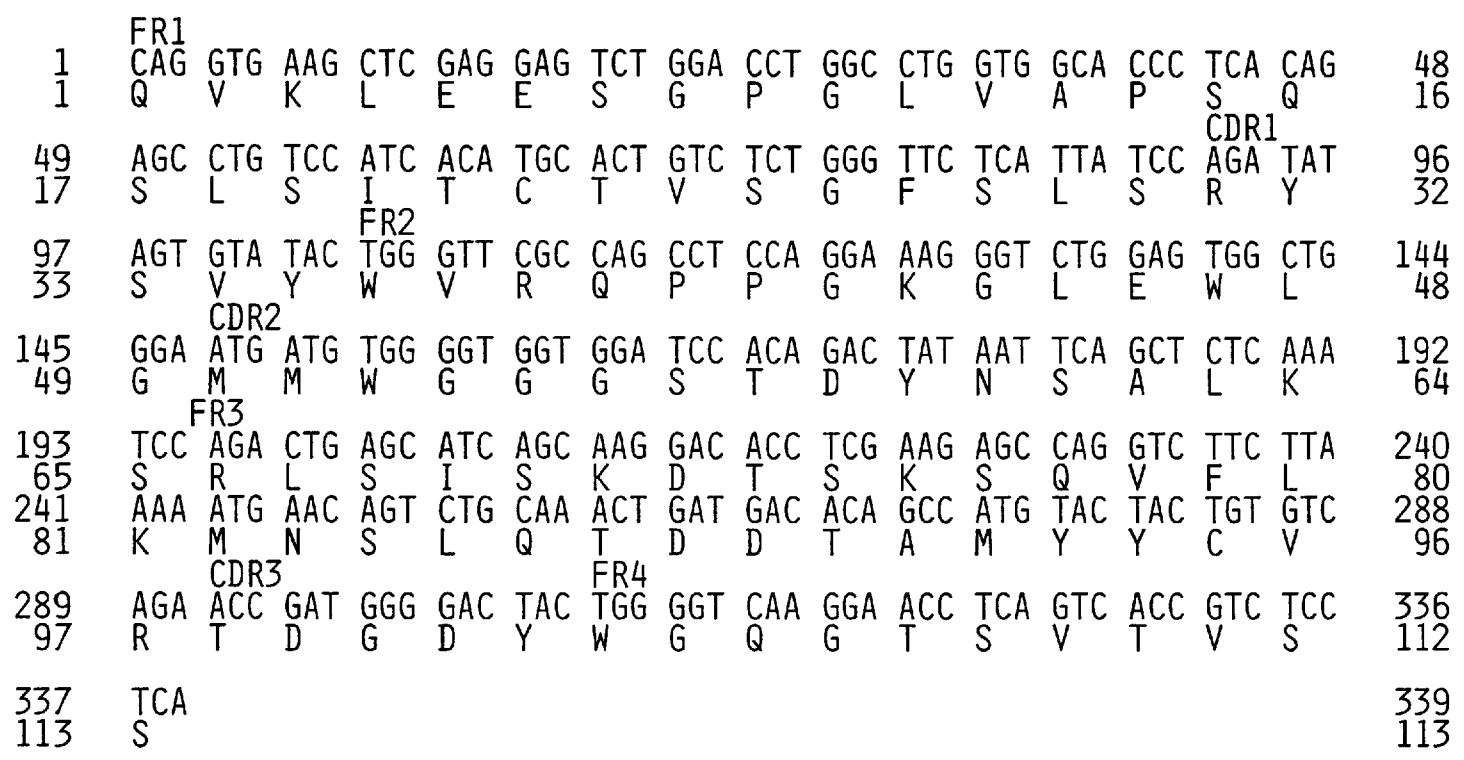

The PCR products were cloned using TA-cloning in a sequencing plasmid. The DNA sequence of several independent clones encoding VH and VL were determined. From these DNA sequences, a consensus amino acid sequence for both the VH and VL regions of the monoclonal antibody 5D12 were deduced. FIGS. 10 and 11 show the cDNA and the deduced protein sequence of the VH and VL regions, respectively of monoclonal antibody 5D12. Also indicated on FIGS. 10 and 11 are the locations of the four framework regions (as FR1, FR2, FR3 and FR4) and the three complementarity determining regions (as CDR1, CDR2, and CDR3) which are positioned therebetween.

The deduced amino acid sequences of the VH and VL regions were used to search different databases for human antibody sequences with the best homology to 5D12. The results of this search comparing ten homologous sequences (H1 to H10) relative to the deduced sequences for the VH and VL regions of 5D12 are shown in Tables 1 and 2, respectively. In particular, in each of Tables 1 and 2, the following information is shown:

a. The first column shows the position of the amino acids, with number one being the first amino acid after cleavage of the signal peptide.
b. The second column shows the four framework (FR) regions, as black shaded areas, or the CDR status of the unshaded areas.
c. The third column shows general data on the 3-dimensional location of the amino acid according to X-ray structure. These amino acids of the framework region that are on the exterior are designated "EX."

TABLE 1

| 5D12 HEAVY CHAIN VARIABLE REGION | | | | M | change to | H1 | H2 | H3 | H4 | H5 | H6 | H7 | H8 | H9 | H10 |
|---|---|---|---|---|---|---|---|---|---|---|---|---|---|---|---|
| 1 | | EX | | Q | | | | | | | | R | | | |
| 2 | | MB | Vernier | V | | | | | | | | L | | | |
| 3 | | EX | | K | Q | Q | Q | Q | Q | Q | N | Q | Q | T | Q |
| 4 | | BU | | L | | | | | | | | | | | |
| 5 | | EX | | E | V | Q | Q | V | V | V | R | V | Q | T | V |
| 6 | | BU | OKT3 | E | | Q | | | D | | | | | | |
| 7 | | EX | | S | | W | T | | | | | | | | |
| 8 | | EX | | G | | | | | | | | | | | |
| 9 | | EX | | P | | A | | G | G | | G | | | | G |
| 10 | | EX | | G | | | | | | A | | | A | | |
| 11 | | EX | | L | | | | | | V | | | V | | |
| 12 | | MB | | V | | | I | | | | | | | | |
| 13 | | ME EX | | A | K | K | R | Q | Q | E | K | Q | K | K | Q |
| 14 | | EX | | P | | | | | A | | | | | | A |
| 15 | | EX | | S | | | | G | G | G | T | G | | K | G |
| 16 | | ME | | Q | | E | | G | G | G | H | R | E | | T |
| 17 | | ME | | S | | T | T | | | T | | | T | P | |
| 18 | | MB | | L | | | | | | | | | | | |
| 19 | | ME EX | | S | | | | R | R | R | T | R | | T | R |
| 20 | | BU | | I | | T | T | L | L | L | L | L | L | L | L |
| 21 | | ME EX | | T | | | | S | S | S | | S | | | S |
| 22 | | BU | | C | | | | | | | | | | | |
| 23 | | EX | OKT3 | T | | A | | A | A | S | | S | I | | |
| 24 | | BU | OKT3 | V | | | | A | A | A | F | S | | F | A |
| 25 | | EX | | S | | F | | | | | | | | | |
| 26 | | EX | can H1 | G | | | | | | | | | | | A |
| 27 | | BU | can H1, Tac, Vernier | F | | G | S | | | | L | | G | | |
| 28 | | EX ME | Vernier | S | | | T | T | T | T | | I | P | | N |
| 29 | | BU | can H1, Vernier | L | | F | F | V | F | F | V | F | I | | |
| 30 | | ME EX | Tac, Vernier | S | | | | | | | N | | R | | |
| 31 | CDR-1 | | | R | | G | N | S | Y | A | T | S | | T | D |
| 32 | | | | Y | | D | H | | N | R | | Y | S | | Y |
| 33 | | | | S | | Y | Y | | N | D | G | A | Y | R | A |
| 34 | | | can H1 | V | | W | Y | M | M | M | M | M | W | M | M |
| 35 | | | | Y | | S | I | S | N | N | S | | | G | R | H |
| 36 | | BU | | W | | | | | | | | | | | |
| 37 | | BU | | V | | I | | | I | | I | I | | | |
| 38 | | BU MB | | R | | | | | | | | | | | |
| 39 | | BU MB | | Q | | | | | | | | | R | | |
| 40 | | EX ME | | P | | | A | V | A | | A | | | | A |
| 41 | | EX | | P | | | | T | | | | | | | |
| 42 | | EX | | G | | | | | | | | | | | |
| 43 | | EX | | K | | R | R | | | | | | | | |
| 44 | | EX | | G | | | A | | A | | | | A | | |
| 45 | | BU | | L | | | | | | | | | | | |
| 46 | | ME | | E | | | Z | | | | | | | | Z |
| 47 | | BU | Venier | W | | | | | | | | | | | |
| 48 | | BU | Tac, Venier | L | | I | I | V | V | | | V | I | | V |
| 49 | | BU | Venier | G | | | | S | S | S | A | A | | A | A |

TABLE 1-continued

| 5D12 HEAVY CHAIN VARIABLE REGION | | | M | change to | H1 | H2 | H3 | H4 | H5 | H6 | H7 | H8 | H9 | H10 |
|---|---|---|---|---|---|---|---|---|---|---|---|---|---|---|
| 50 | CDR-2 | | M | | | | | | | | | | | |
| 51 | | | M | | | | | | | | | | | |
| 52 | | | W | | | | | | | | | | | |
| 52A | | Can H2-2 | G | | | | | | | | | | | |
| 53 | | | G | | | | | | | | | | | |
| 54 | | CAN H2-3, 4 | G | | | | | | | | | | | |
| 55 | | Can H2-1, 2, 4 interacts with 71 | S | | | | | | | | | | | |
| 56 | | | T | | | | | | | | | | | |
| 57 | | | D | | | | | | | | | | | |
| 58 | | | Y | | | | | | | | | | | |
| 59 | | | N | | | | | | | | | | | |
| 60 | | | S | | | | | | | | | | | |
| 61 | | | A | | | | | | | | | | | |
| 62 | | | L | | | | | | | | | | | |
| 63 | | | K | | | | | | | | | | | |
| 64 | | | S | | | | | | | | | | | |
| 65 | | | - | | | | | | | | | | | |
| 66 | MB PB | ErbB2, Tac | R | | V | V | F | F | F | | F | V | | F |
| 67 | BU | Tac, Venier | L | | | | | | | | | | | |
| 68 | EX | | S | T | T | T | T | T | T | T | T | | | T |
| 69 | BU | Venier | I | | | M | | | | | | | | |
| 70 | ME | | S | | L | | | | | | | | | |
| 71 | BU | Can H2-2, 3, 4 interacts with 55, ErB2 | K | | | V | R | R | R | K | R | V | K | R |
| 72 | ME PB | | D | | | | N | N | | | | | N | B |
| 73 | PB EX | ErbB2, Venier | T | | | D | D | B | | N | | D | I | |
| 74 | EX | | S | | | | | | | | | | | |
| 75 | EX | | K | | | R | | | | | R | | | |
| 76 | ME | | S | N | N | N | B | N | N | N | N | N | N | B |
| 77 | PB MB | | Q | | L | | T | T | S | | T | | | T |
| 78 | BU | ErbB2, Venier | V | | F | F | | L | L | | L | F | | L |
| 79 | PB MB | | F | | S | S | V | Y | Y | V | | S | V | Y |
| 80 | BU | | L | | | | | | | | | | | |
| 81 | PB ME | | K | | | R | Q | N | Q | | Q | N | I | Z |
| 82 | BU | | M | | L | L | | | | V | | L | | |
| 82A | ME PB | | N | | S | S | B | | S | T | D | R | I | K |
| 82B | EX | | S | | | | | | | N | | | N | T |
| 82C | BU | | L | | V | V | | | M | | M | V | | |
| 83 | ME | | Q | R | T | T | R | R | D | R | S | N | | R |
| 84 | ME EX | | T | A | A | A | A | A | P | P | A | P | | |
| 85 | EX | | D | E | A | A | E | E | E | A | E | A | V | E |
| 86 | BU | | D | | | | | | | | | | | |
| 87 | PB EX | | T | | | | | | | | | | | |
| 88 | EX BU | | A | | | | | | | G | | | | |
| 89 | PB ME | Tac | M | | V | V | V | V | V | T | V | | T | V |
| 90 | BU | | Y | | | | | | | | | | | |
| 91 | BU | Tac | Y | | | | | | | F | | | | |
| 92 | BU | | C | | | | | | | | | | | |
| 93 | BU | ErbB2, Venier | V | | A | A | A | A | A | A | A | A | A | A |
| 94 | BU | Can H1, Tac, see 101 | R | | | | | | | | | | | K |
| 95 | CDR-3 | | T | | | | | | | | | | | |
| 96 | | | N | | | | | | | | | | | |
| 97 | | | G | | | | | | | | | | | |
| 98 | | | - | | | | | | | | | | | |
| 99 | | | - | | | | | | | | | | | |
| 100 | | | - | | | | | | | | | | | |
| 100A | | | - | | | | | | | | | | | |
| 100B | | | - | | | | | | | | | | | |
| 100C | | | - | | | | | | | | | | | |
| 100D | | | - | | | | | | | | | | | |
| 100E | | | - | | | | | | | | | | | |
| 100F | | | - | | | | | | | | | | | |
| 100G | | | - | | | | | | | | | | | |
| 100H | | | - | | | | | | | | | | | |
| 100I | | | - | | | | | | | | | | | |
| 100J | | | - | | | | | | | | | | | |
| 100K | | | - | | | | | | | | | | | |
| 101 | | D/E may bridge with R/K at 94 | D | | | | | | | | | | | |
| 102 | | | Y | | | | | | | | | | | |

TABLE 1-continued

| 5D12 HEAVY CHAIN VARIABLE REGION | | | M | H1 | H2 | H3 | H4 | H5 | H6 | H7 | H8 | H9 | H10 |
|---|---|---|---|---|---|---|---|---|---|---|---|---|---|
| 103 | BU | Tac, Venier | W | | | F | | | | | | | |
| 104 | BU EX | Tac | G | | | | | | | | | | |
| 105 | EX | Tac | Q | | | | K | | | | | K | |
| 106 | BU | | G | | | | | | | | | | |
| 107 | MB | Tac | T | | S | | | | | | | | |
| 108 | EX ME | | S | T | | T | L | T | L | L | W | P | T | T | L |
| 109 | BU | | V | | | | | - | S | | | | |
| 110 | ME | | T | | | | | - | P | | H | | |
| 111 | BU | | V | | | | | - | S | | | | |
| 112 | EX ME | | S | | | | | - | L | | | | |
| 113 | EX | | S | | | | | - | Q | | | | L |

TABLE 2

| 5D12 HEAVY CHAIN VARIABLE REGION | | | M | change to | H1 | H2 | H3 | H4 | H5 | H6 | H7 | H8 | H9 | H10 |
|---|---|---|---|---|---|---|---|---|---|---|---|---|---|---|
| 1 | EX | | E | D | D | D | D | D | D | D | D | D | E |
| 2 | BU | Can L1, Venier | L | | V | I | I | V | I | I | I | I | I |
| 3 | EX | | Q | | V | V | V | V | V | V | V | V | V |
| 4 | BU | Venier | L | | M | M | M | M | M | | M | M | M |
| 5 | ME EX | | T | | | | | | | | | | |
| 6 | BU | | Q | | | | | | | | | | |
| 7 | EX | | S | | | | | | T | | | | |
| 8 | ME | | P | | | | | | | | | | |
| 9 | EX | | L | | | | | | | | N | D | D | G |
| 10 | EX | | S | | | | | F | | | | | T |
| 11 | MB | | L | | | | | | | | | | |
| 12 | PB | | P | | | | | | | | A | A | A | S |
| 13 | BU | | V | | | | | | | | | | |
| 14 | ME | | S | | T | T | T | T | T | T | | | |
| 15 | ME EX | | L | | P | P | | P | P | | | | P |
| 16 | EX | | G | | | | | | | | | | |
| 17 | ME | | D | | Q | E | E | E | E | E | E | E | E |
| 18 | ME EX | | Q | R | P | P | P | P | P | P | R | R | R | R |
| 19 | MB | | A | | | | | | | | | | |
| 20 | ME | | S | | | | | | | | T | T | T | T |
| 21 | BU | | I | | | | | | | | | | L |
| 22 | ME | | S | | | | | Q | | | N | N | N |
| 23 | BU | | C | | | | | | | | | | |
| 24 | CDR-1 | | R | | | | | | | | K | K | K |
| 25 | | Can L1 | S | | | | | | | | | | A |
| 26 | | | S | | | | | | | | | | |
| 27 | | | Q | | | | | | | | | | |
| 28 | | | S | | | | | | | N | | | |
| 28A | | | - | | | | | | | | V | I | V |
| 29 | | Can L1 | L | | | | | | | | | | |
| 30 | | | V | | L | L | | L | L | | Y | Y | Y |
| 31 | | | N | | Y | H | H | Y | D | Z | S | M | S | S |
| 31A | | | S | | | | R | | | | | | |
| 31B | | | - | | | | | G | | | | | |
| 32 | | | N | | D | | D | B | D | B | | D | |
| 33 | | Can L1 | G | | | Y | P | B | | | S | N | N |
| 34 | | | N | | Y | P | B | | | K | K | K | |
| | | | T | | N | D | | | B | N | N | N | S |
| | | | Y | | | | | | | | | | |
| | | | L | | | | | | | | | | |
| | | | H | | N | D | N | B | N | D | A | A | A | A |

TABLE 2-continued

| 5D12 HEAVY CHAIN VARIABLE REGION | | | M | change to | H1 | H2 | H3 | H4 | H5 | H6 | H7 | H8 | H9 | H10 |
|---|---|---|---|---|---|---|---|---|---|---|---|---|---|---|
| 35 | | BU | Venier | W | | | | | | | | | | |
| 36 | | BU | Venier | Y | F | | | | | | | | | |
| 37 | | BU | | L | Q | | | | | | Q | Q | Q | Q |
| 38 | | MB | | Q | | | | | | Z | | | | |
| 39 | | ME | | K | R | | | | | | | | | |
| 40 | | EX | | P | | | | A | | | | | | |
| 41 | | EX | | G | | Q | | | | | | | | |
| 42 | | EX | | Q | | | | | Z | | | | | |
| 43 | | MB | | S | | | | | | | P | P | P | A |
| 44 | | BU | | P | | | | | | | | | | |
| 45 | | EX | | K | R | Q | Z | E | Q | Z | | | | R |
| 46 | | PB | OKT3, Venier | L | R | | | | | | | | | |
| 47 | | BU | OKT3, Venier | L | | | | | | | | | | |
| 48 | | BU | Can L2, Venier | I | | | | | | | | | | |
| 49 | | PB | Venier | Y | | | | | | | | | | |
| 50 | CDR-2 | | | K | L | A | L | T | L | W | W | W | W | G |
| 51 | | | | V | G | I | S | L | G | A | A | A | A | A |
| 52 | | | | S | | | | | | | | | | |
| 53 | | | | N | | | | | | Y | Y | T | T | S |
| 54 | | | | R | | | | | | | | | | |
| 55 | | | ErbB2 | F | D | A | A | D | A | A | L | L | L | A |
| 56 | | | | S | | | | | | | | | | T |
| 57 | | EX | | G | | | | | | | | | | |
| 58 | | BU | | V | | | | | | | | | | I |
| 59 | | ME | | P | | | | | | | | | | |
| 60 | | EX | | D | | | | | | N | | | | |
| 61 | | MB | | R | | | | | | | | | | |
| 62 | | BU | | F | | | | | | | | | | |
| 63 | | EX | Tac | S | | | | | | | | | | |
| 64 | | BU | Can L2, Venier | G | | | | D | | | | | | |
| 65 | | EX | | S | | | | | | | | | | |
| 66 | | EX | ErbB2, Venier | G | | | | | | | | | | |
| 67 | | EX | | S | | | | | | | | | | |
| 68 | | EX | Venier | G | | | | | | | | | | |
| 69 | | ME | Venier | T | | | | | | | | | | |
| 70 | | EX | | D | | | | | | | B | | | |
| 71 | | BU | Can L1, Venier | F | | | | | | | | | | |
| 72 | | ME | | T | | | | | | | | | | |
| 73 | | BU | | L | | | | | | | | | | |
| 74 | | PB | | K | | | | | | | T | T | T | T |
| 75 | | BU | | I | | | | | | | | | | |
| 76 | | EX | | S | | | | T | | | | | | |
| 77 | | EX | | R | | | | | | | S | S | S | |
| 78 | | BU | | V | | | | | | | L | L | L | L |
| 79 | | ME | | E | | | Q | Q | Z | Q | Q | Q | | |
| 80 | | EX | | A | | | | | | | | | | P |
| 81 | | EX | | E | | | | | | Z | | | | X |
| 82 | | BU | | D | | | | | | | B | | | |
| 83 | | PB | | L | V | | V | V | V | V | V | V | V | F |
| 84 | | BU | | G | | | | | | | A | A | A | A |
| 85 | | PB | | V | | | | | | | | | | |
| 86 | | BU | | Y | | | | | | | | | | |
| 87 | | BU | | F | Y | Y | Y | Y | Y | Y | Y | Y | Y | Y |
| 88 | | BU | | C | | | | | | | | | | |

TABLE 2-continued

| 5D12 HEAVY CHAIN VARIABLE REGION | | | M | change to | H1 | H2 | H3 | H4 | H5 | H6 | H7 | H8 | H9 | H10 |
|---|---|---|---|---|---|---|---|---|---|---|---|---|---|---|
| 89 | | CDR-3 | S | | M | M | M | M | M | Q | Q | Q | Q | |
| 90 | | Can L3 | Q | | | | Z | | | | | | | |
| 91 | | | S | | G | G | A | A | R | A | Y | Y | Y | Y |
| 92 | | | T | | I | I | I | I | I | Y | Y | D | Q | |
| 93 | | | H | | Q | Q | Z | I | Q | S | N | T | S | |
| 94 | | Can L3-2 | V | | W | T | A | S | T | T | I | I | S | |
| 95 | | Can L3-1, 3 | P | | S | | | | | | | | | |
| 96 | | | W | | Q | I | Y | Y | I | Y | | | | |
| 97 | | | T | | | | | | | | S | | | |
| 98 | BU | Venier | F | | | | | | | | | | | |
| 99 | EX | | G | | | | | | | | | | | |
| 100 | EX | | G | | Q | Q | Q | Q | Q | | Q | Q | | Q |
| 101 | BU | | G | | | | | | | | | | | |
| 102 | BU | | T | | | | | | | | | | | |
| 103 | ME | | K | | | | | R | | | N | | | |
| 104 | BU | | L | | V | V | | | | V | | V | V | V |
| 105 | EX | | E | | | | | Z | | | | | | |
| 106 | PB | | I | | | | | | | | | | | |
| 107 | ME | | K | | | | | | R | | | | | | d. The fourth column identifies canonical residues (Can, followed by its Hn or Ln loop association). Vernier indicates amino acids in the immediately adjacent layers supporting the CDRs. In addition, ErbB2, Tac and OKT3 indicate amino acid positions that were profitably changed back to mouse after complete CDR grafting of the respective monoclonal antibodies.

e. The fifth column shows the VH or VL sequence of 5D12, using conventional single letter nomenclature for the various amino acid residues.

f. The sixth column indicates the amino acid changes that were made to the mouse 5D12 sequence to humanize the antibody.

g. The next ten columns (7–16), designated as H1 to H10, show the most homologous human antibody sequences that came out of the data base searches. Shaded cells in columns 7–16 indicate amino acid residues in the CDR regions of the closest human proteins that were not changed. Empty cells indicate that the human and the mouse amino acid are the same.

The choice of mouse residues reported in the fifth column that were changed, as per the sixth column of each Table, was based upon all the data present in the respective Table. In particular, it was decided that nine (9) residues be changed in the VH region and four (4) residues be charged in the VL region. (See Tables 1 and 2 at column 6).

The next step in the humanization process of 5D12 was to design mutagenesis primers to change the indicated residues from mouse to human. From the plasmids containing the VH or VL mouse variable regions, single stranded DNA was made by infection with R408 helper phage, followed by annealing of the mutagenesis primers. Double stranded DNA was made by T4 DNA polymerase and T4 DNA ligase together with dNTPs. Several clones were sequenced to find a clone containing all of the introduced mutations. FIGS. 12 and 13 show the cDNA and the deduced amino acid sequence of the humanized VH and VL regions, respectively, now designated as $VH_x$ and $VL_x$, respectively.

Figure 14:
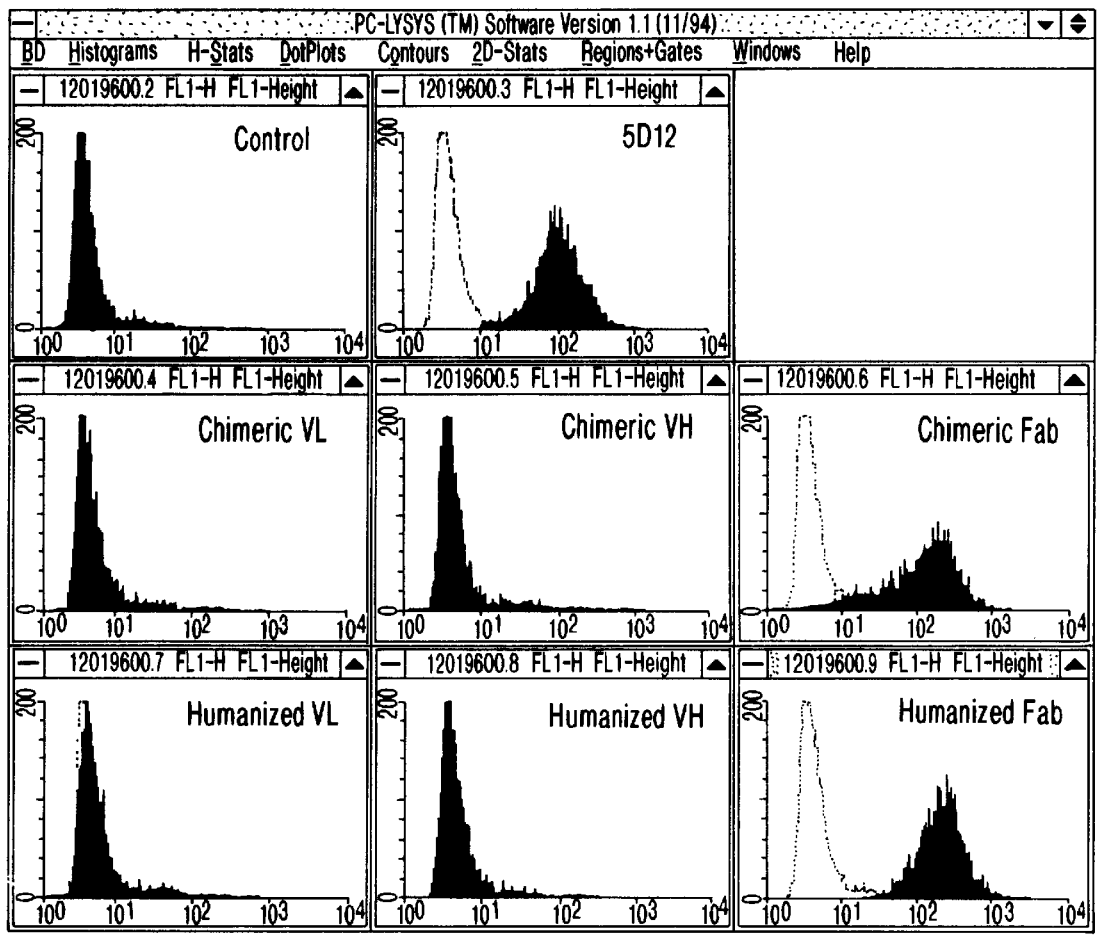
FIG. 14 compares the binding to CD40 expressing cells by murine 5D12 monoclonal antibody, chimeric 5D12 Fab, chimeric VL, chimeric VH, humanized VL, humanized VH, and humanized 5D12 Fab, via FACScan flow cytometer curves, relative to each other and to FITC-conjugate as the control.

To obtain humanized Fab fragments of 5D12, the two humanized variable regions ($VH_x$ and $VL_x$) were each cloned in a baculovirus (AcNPV) expression plasmid (see Example 1B) that included part of the constant region of the human IgG, heavy chain ($CH_H$) and the complete human constant light ($CL_H$) region respectively, thereby producing expression vectors encoding $VH_xCH_H$ and $VL_xCL_H$, respectively. The two expression vectors from above, encoding $VH_xCH_H$ and $VL_xCL_H$ were cotransfected with wildtype AcNPV baculovirus into Sf9 insect cells (see Example 1B) followed by a few rounds of amplification to obtain high titer recombinant virus stocks. To express the humanized 5D12 Fab fragment, the Sf9 cells were infected with the humanized light and heavy chain recombinant virus stocks for four days. The supernatants and lysates were analyzed for humanized 5D12 Fab expression using Western blotting and FACS analysis (FIG. 14). In the resulting 5D12 Fab fragment, the light chain had 223 amino acid residues, and the heavy chain had 239 amino acid residues.

Similarly, a human/mouse chimeric 5D12 Fab fragment was produced. In particular, the cDNA encoding the two mouse variable regions ($VH_M$ and $VL_M$) of 5D12, as obtained above, were each cloned in a baculovirus (AcNPV) expression plasmid (see Example 1B) that includes a portion of the constant region of the human IgG heavy chain ($CH_H$) and the complete constant light ($CL_H$) region respectively, thereby producing expression vectors encoding $VH_MCH_H$ and $VL_M$ $CL_H$, respectively. The two expression vectors encoding $VH_MCH_H$ and $VL_MCL_H$ were cotransfected with wildtype AcNPV baculovirus into Sf9 insect cells (see Example 1B) followed by a few rounds of amplification to obtain high titer recombinant virus stocks. To express the chimeric human/mouse 5D12 Fab fragment, the Sf9 cells were infected with the chimeric heavy and light chain recombinant virus stocks for four days. The supernatants and lysates were analyzed for chimeric 5D12 Fab expression using Western blotting and FACS analysis (FIG. 14).

Western Blot

A Western blot of an SDS-PAGE 10% gel, which was run under non-reducing conditions, was stained with 4-chloro-naphthol. Lanes 1 and 5, which were samples of culture supernatants from Sf9 cells infected with humanized 5D12 Fab fragment and chimeric 5D12 Fab fragment, showed comparable migration across from the 44 kD marker. Lanes 3 and 7, which were samples of culture supernatants from Sf9 cells infected with humanized light chain ($VL_xCL_H$) and chimeric light chain ($VL_M$ $CL_H$ also showed comparable migration that reflected a molecular weight substantially below the 32 kD marker.

FACS Binding Analysis

Using the few cytometric assay techniques disclosed therein, the binding of the anti-human CD40 5D12 monoclonal antibody and the various expressed Fab fragments was determined relative to the B-cell line JY, which expresses high levels of CD40. Cells (500,000/pellet) were incubated with 1 μg 5D12 in a volume of 100 μl or with 100 μl Sf9 culture supernatant (which contained the VL, VH or Fab fragments) for thirty min. at 4° C. After washing with PBS, the cells were incubated with FITC labelled antibodies directed either against murine Ig or against the Fab fragments. Subsequently, the cells were washed and fixed in 0.5% paraformaldehyde in PBS. The cells were analyzed on a FACScan flow cytometer (Becton-Dickson). The results, which are shown in FIG. 14, reflect that with the "humanized" 5D12 Fab fragment and the "chimeric" 5D12 Fab fragment bound to the CD40 antigen on the B cells comparable to the intact 5D12 murine monoclonal antibody, and that the chimeric VL and EL fragments, and the humanized VL and HL fragments exhibited binding that was indistinguishable from that of the non-binding control (i.e., FITC-conjugate only).

FACS Competition Experiment

Figure 15:
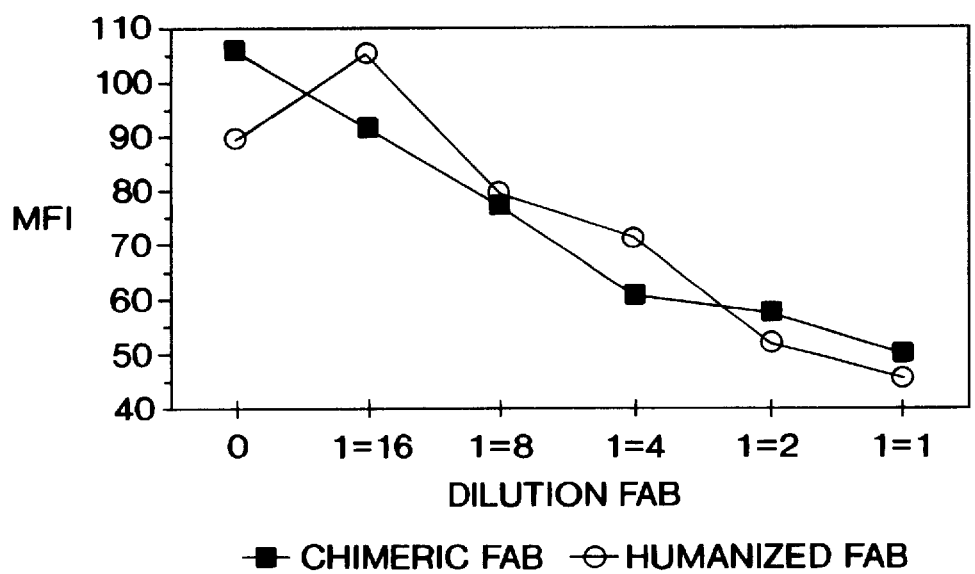
FIG. 15 is a comparative plot of mean fluorescent intensity (MFI) versus Fab dilutions (1=16, 1=8, 1=4, 1=2 and 1=1) of chimeric 5D12 Fab (solid rectangle) and humanized 5D12 Fab (open ovals). To obtain the curve points, a CD40 expressing B cells (JY cell line) was incubated with 50 ng of intact 5D12 monoclonal antibody together with the diluted amounts of the expressed chimeric or humanized 5D12 Fab in 100 μl for thirty minutes at 4° C., and the MFI was measured. The 1=1 dilution, which contained 70 ng chimeric 5D12 Fab or 80 ng humanized 5D12 Fab, was able to inhibit 50% of the intact murine 5D12 monoclonal antibody.

JY cells (250,000/pellet) expressing CD40 were incubated with 50 ng intact 5D12 together with different amounts of the expressed chimeric or humanized 5D12 Fab in 100 μl for thirty minutes at 4° C. The 1=1 dilution contained 70 ng chimeric 5D12 Fab or 80 ng humanized 5D12 Fab (Fab concentration was determined with a sandwich ELISA using goat anti-human IgG as coating, human IgG Fab fragment from Jackson as standard and phosphatase labelled goat anti-human IgG F(ab')$_2$ as detection antibody). After washing with PBS, the cells were incubated with FITC labelled anti-murine Ig, which does not crossreact with the expressed Fab fragments, followed by fixation in 0.5% paraformaldehyde. Cells were analyzed on a FACScan flow cytometer (Becton-Dickinson). The mean fluorescence intensity (MFI) was plotted against the amount of added Fab fragment expressed as a dilution, and is shown in FIG. 15. In the above FACS competition experiment, the chimeric 5D12 fragment and the humanized 5D12 Fab showed the same competitive binding characteristics relative to the parent murine 5D12 monoclonal antibody. See FIG. 15. About 70–80 ng of the Fab fragment (humanized or chimeric) was found to inhibit 50% binding of the whole murine 5D12 antibody (50 ng). See FIG. 15.

Deposition of Cultures

The hybridomas used in the above examples, to illustrate the method of the present invention were deposited in and accepted by the American Type Culture Collection (ATCC), 12301 Parklawn Drive, Rockville, Md., USA, under the terms of the Budapest Treaty.

| Hybridoma | Deposit Date | Accession No. |
| --- | --- | --- |
| B7-24 | May 6, 1993 | HB 11341 |
| 3C6 | May 6, 1993 | HB 11340 |
| 5D12 | May 6, 1993 | HB 11339 |
| 3A8 | January 30, 1996 | HB 12024 |

The present invention has been described with reference to specific embodiments. However, this application is intended to cover those changes and substitutions which may be made by those skilled in the art without departing from the spirit and the scope of the appended claims.

---

We claim:

1. A humanized monoclonal antibody which binds to a human CD40 antigen located on the surface of a normal human B cell, said monoclonal antibody being free of significant agonistic activity, wherein the binding of the antibody to the CD40 antigen inhibits the growth or differentiation of said normal human B cell.

2. The humanized monoclonal antibody of claim 1 selected from the group consisting of humanized 5D12, 3A8 3C6 and a humanized antigen-specific binding fragment thereof, wherein monoclonal antibodies 5D 12, 3A8 and 3C6 are secreted by hybridomas having ATCC Accession Nos. HB 11339, HB 12024 and HB 11340, respectively.

3. The humanized monoclonal antibody of claim 2 which is humanized 5D12 or a humanized antigen-specific binding fragment thereof.

4. The humanized monoclonal antibody of claim 2 which is humanized 3A8 or a humanized antigen-specific binding fragment thereof.

5. The humanized monoclonal antibody of claim 2 which is humanized 3C6 or a humanized antigen-specific binding fragment thereof.

6. A composition comprising:
(i) a humanized monoclonal antibody which binds to a human CD40 antigen located on the surface of a normal human B cell, said monoclonal antibody being free of significant agonistic activity, and wherein the binding of the antibody to the CD40 antigen inhibits the growth or differentiation of said normal human B cell; and
(ii) an acceptable excipient.

7. The composition of claim 6, wherein the humanized monoclonal antibody is selected from the group consisting of humanized 5D12, 3A8, 3C6 and a humanized antigen-specific binding fragment thereof, wherein monoclonal antibodies 5D12, 3A8 and 3C6 are secreted by hybridomas having ATCC Accession Nos. HB11339, HB 12024 and HB 11340, respectively.

8. The composition of claim 7, wherein the humanized monoclonal antibody is humanized 5D12 or a humanized antigen-specific binding fragment thereof.

9. The composition of claim 7, wherein the humanized monoclonal antibody is humanized 3A8 or a humanized antigen-specific binding fragment thereof.

10. The composition of claim 7, wherein the humanized monoclonal antibody is humanized 3C6 or a humanized antigen-specific binding fragment thereof.

11. A pharmaceutical composition comprising:
(i) a humanized monoclonal antibody which binds to a human CD40 antigen located on the surface of a normal human B cell, said monoclonal antibody being free of significant agonistic activity, wherein the binding of the antibody to the CD40 antigen inhibits the growth or differentiation of said normal human B cell; and
(ii) a pharmaceutically acceptable excipient.

12. The pharmaceutical composition of claim 11, wherein the humanized monoclonal antibody is selected from the group consisting of humanized 5D12, 3A8, 3C6 and a humanized antigen-specific binding fragment thereof, and wherein monoclonal antibodies 5D12, 3A8 and 3C6 are secreted by hybridornas having ATCC Accession Nos. HB11339, HB 12024 and HR 11340, respectively.

13. The pharmaceutical composition of claim 12, wherein the humanized monoclonal antibody is humanized 5D12 or a humanized antigen-specific binding fragment thereof.

14. The pharmaceutical composition of claim 12, wherein the humanized monoclonal antibody is humanized 3A8 or a humanized antigen-specific binding fragment thereof.

15. The pharmaceutical composition of claim 12, wherein the humanized monoclonal antibody is humanized 3C6 or a humanized antigen-specific binding fragment thereof.

16. A method for treating systemic lupus erythematosus in a patient, the method comprising administering to a patient in need of such treatment a composition comprising:
(i) a therapeutically effective amount of a humanized monoclonal antibody which binds to a human CD40 antigen located on the surface of a normal human B cell, said monoclonal antibody being free of significant agonistic activity, wherein the binding of the antibody to the CD40 antigen inhibits the growth or differentiation of said normal human B cell; and
(ii) a pharmaceutically acceptable excipient.

17. The method of claim 16 wherein the monoclonal antibody is selected from the group consisting of humanized 5D12, 3A8, 3C6 and a humanized antigen-specific binding fragment thereof, wherein monoclonal antibodies 5D12, 3A8 and 3C6 are secreted by hybridomas having ATCC Accession Nos. HB 11339, HB 12024 and HB 11340, respectively.

18. The method of claim 17 wherein the monoclonal antibody is humanized 5D12 or a humanized antigen-specific binding fragment thereof.

19. The method of claim 17 wherein the monoclonal antibody is humanized 3A8 or a humanized antigen-specific binding fragment thereof.

20. The method of claim 17 wherein the monoclonal antibody is humanized 3C6 or a humanized antigen-specific binding fragment thereof.

* * * * *

UNITED STATES PATENT AND TRADEMARK OFFICE
CERTIFICATE OF CORRECTION

PATENT NO.   :   5,874,082
DATED        :   February 23, 1999
INVENTOR(S)  :   de Boer It is certified that error appears in the above-identified patent and that said Letters Patent is hereby corrected as shown below:

Title page;

item [*],   delete "Nos. 5,667,165 and" and substitute therefor --No.--.

At col. 39, line 57, delete "5D 12" and substitute therefor --5D12--.

Signed and Sealed this

Twenty-fourth Day of August, 1999

Attest:

Q. TODD DICKINSON

*Attesting Officer*      *Acting Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 339 base pairs
        ( B ) TYPE: nucleic acid
        ( C ) STRANDEDNESS: single
        ( D ) TOPOLOGY: linear ( i i ) MOLECULE TYPE: Protein ( i x ) FEATURE:
        ( A ) NAME/KEY: CDS
        ( B ) LOCATION: 1..339

( x i ) SEQUENCE DESCRIPTION: SEQ ID NO:1:

```
CAG  GTG  AAG  CTC  GAG  GAG  TCT  GGA  CCT  GGC  CTG  GTG  GCA  CCC  TCA  CAG      4 8
Gln  Val  Lys  Leu  Glu  Glu  Ser  Gly  Pro  Gly  Leu  Val  Ala  Pro  Ser  Gln
 1               5                        10                      15

AGC  CTG  TCC  ATC  ACA  TGC  ACT  GTC  TCT  GGG  TTC  TCA  TTA  TCC  AGA  TAT      9 6
Ser  Leu  Ser  Ile  Thr  Cys  Thr  Val  Ser  Gly  Phe  Ser  Leu  Ser  Arg  Tyr
                 20                       25                      30

AGT  GTA  TAC  TGG  GTT  CGC  CAG  CCT  CCA  GGA  AAG  GGT  CTG  GAG  TGG  CTG     144
Ser  Val  Tyr  Trp  Val  Arg  Gln  Pro  Pro  Gly  Lys  Gly  Leu  Glu  Trp  Leu
             35                       40                       45
```

| | | | | | | | | | | | | | | | | |
|---|---|---|---|---|---|---|---|---|---|---|---|---|---|---|---|---|
| GGA | ATG | ATG | TGG | GGT | GGT | GGA | TCC | ACA | GAC | TAT | AAT | TCA | GCT | CTC | AAA | 192 |
| Gly | Met | Met | Trp | Gly | Gly | Gly | Ser | Thr | Asp | Tyr | Asn | Ser | Ala | Leu | Lys | |
| | 50 | | | | 55 | | | | | 60 | | | | | | |
| TCC | AGA | CTG | AGC | ATC | AGC | AAG | GAC | ACC | TCG | AAG | AGC | CAG | GTC | TTC | TTA | 240 |
| Ser | Arg | Leu | Ser | Ile | Ser | Lys | Asp | Thr | Ser | Lys | Ser | Gln | Val | Phe | Leu | |
| 65 | | | | | 70 | | | | | 75 | | | | | 80 | |
| AAA | ATG | AAC | AGT | CTG | CAA | ACT | GAT | GAC | ACA | GCC | ATG | TAC | TAC | TGT | GTC | 288 |
| Lys | Met | Asn | Ser | Leu | Gln | Thr | Asp | Asp | Thr | Ala | Met | Tyr | Tyr | Cys | Val | |
| | | | | 85 | | | | | 90 | | | | | 95 | | |
| AGA | ACC | GAT | GGG | GAC | TAC | TGG | GGT | CAA | GGA | ACC | TCA | GTC | ACC | GTC | TCC | 336 |
| Arg | Thr | Asp | Gly | Asp | Tyr | Trp | Gly | Gln | Gly | Thr | Ser | Val | Thr | Val | Ser | |
| | | | 100 | | | | | 105 | | | | | 110 | | | |
| TCA | | | | | | | | | | | | | | | | 339 |
| Ser | | | | | | | | | | | | | | | | |

(2) INFORMATION FOR SEQ ID NO:2:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | | |
|---|---|---|---|---|---|---|---|---|---|---|---|---|---|---|---|
| Gln | Val | Lys | Leu | Glu | Glu | Ser | Gly | Pro | Gly | Leu | Val | Ala | Pro | Ser | Gln |
| 1 | | | | 5 | | | | | 10 | | | | | 15 | |
| Ser | Leu | Ser | Ile | Thr | Cys | Thr | Val | Ser | Gly | Phe | Ser | Leu | Ser | Arg | Tyr |
| | | | 20 | | | | | 25 | | | | | 30 | | |
| Ser | Val | Tyr | Trp | Val | Arg | Gln | Pro | Pro | Gly | Lys | Gly | Leu | Glu | Trp | Leu |
| | | | 35 | | | | 40 | | | | | 45 | | | |
| Gly | Met | Met | Trp | Gly | Gly | Gly | Ser | Thr | Asp | Tyr | Asn | Ser | Ala | Leu | Lys |
| | 50 | | | | 55 | | | | | 60 | | | | | |
| Ser | Arg | Leu | Ser | Ile | Ser | Lys | Asp | Thr | Ser | Lys | Ser | Gln | Val | Phe | Leu |
| 65 | | | | | 70 | | | | | 75 | | | | | 80 |
| Lys | Met | Asn | Ser | Leu | Gln | Thr | Asp | Asp | Thr | Ala | Met | Tyr | Tyr | Cys | Val |
| | | | | 85 | | | | | 90 | | | | | 95 | |
| Arg | Thr | Asp | Gly | Asp | Tyr | Trp | Gly | Gln | Gly | Thr | Ser | Val | Thr | Val | Ser |
| | | | 100 | | | | | 105 | | | | | 110 | | |
| Ser | | | | | | | | | | | | | | | |

(2) INFORMATION FOR SEQ ID NO:3:

(i) SEQUENCE CHARACTERISTICS:
        (A) LENGTH: 336 base pairs
        (B) TYPE: nucleic acid
        (C) STRANDEDNESS: single
        (D) TOPOLOGY: linear (ii) MOLECULE TYPE: Protein (ix) FEATURE:
        (A) NAME/KEY: CDS
        (B) LOCATION: 1..336

(xi) SEQUENCE DESCRIPTION: SEQ ID NO:3:

| | | | | | | | | | | | | | | | | |
|---|---|---|---|---|---|---|---|---|---|---|---|---|---|---|---|---|
| GAG | CTC | CAG | CTG | ACC | CAG | TCT | CCA | CTC | TCC | CTG | CCT | GTC | AGT | CTT | GGA | 48 |
| Glu | Leu | Gln | Leu | Thr | Gln | Ser | Pro | Leu | Ser | Leu | Pro | Val | Ser | Leu | Gly | |
| 115 | | | | | 120 | | | | | 125 | | | | | | |
| GAT | CAA | GCC | TCC | ATC | TCT | TGC | AGA | TCT | AGT | CAG | AGC | CTT | GTA | AAC | AGT | 96 |
| Asp | Gln | Ala | Ser | Ile | Ser | Cys | Arg | Ser | Ser | Gln | Ser | Leu | Val | Asn | Ser | |
| 130 | | | | | 135 | | | | | 140 | | | | | 145 | |
| AAT | GGA | AAC | ACC | TAT | TTA | CAT | TGG | TAC | CTG | CAG | AAG | CCA | GGC | CAG | TCT | 144 |

```
Asn  Gly  Asn  Thr  Tyr  Leu  His  Trp  Tyr  Leu  Gln  Lys  Pro  Gly  Gln  Ser
               150                      155                      160

CCA  AAG  CTC  CTG  ATC  TAC  AAA  GTT  TCC  AAC  CGA  TTT  TCT  GGG  GTC  CCA     192
Pro  Lys  Leu  Leu  Ile  Tyr  Lys  Val  Ser  Asn  Arg  Phe  Ser  Gly  Val  Pro
               165                      170                      175

GAC  AGG  TTC  AGT  GGC  AGT  GGA  TCA  GGG  ACA  GAT  TTC  ACA  CTC  AAG  ATC     240
Asp  Arg  Phe  Ser  Gly  Ser  Gly  Ser  Gly  Thr  Asp  Phe  Thr  Leu  Lys  Ile
               180                      185                      190

AGC  AGA  GTG  GAG  GCT  GAG  GAT  CTG  GGA  GTT  TAT  TTC  TGC  TCT  CAA  AGT     288
Ser  Arg  Val  Glu  Ala  Glu  Asp  Leu  Gly  Val  Tyr  Phe  Cys  Ser  Gln  Ser
          195                      200                      205

ACA  CAT  GTT  CCG  TGG  ACG  TTC  GGT  GGA  GGC  ACC  AAG  CTG  GAA  ATC  AAA     336
Thr  His  Val  Pro  Trp  Thr  Phe  Gly  Gly  Gly  Thr  Lys  Leu  Glu  Ile  Lys
210                      215                      220                      225
```

( 2 ) INFORMATION FOR SEQ ID NO:4:

( i ) SEQUENCE CHARACTERISTICS:
        ( A ) LENGTH: 112 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Glu  Leu  Gln  Leu  Thr  Gln  Ser  Pro  Leu  Ser  Leu  Pro  Val  Ser  Leu  Gly
 1                  5                        10                      15

Asp  Gln  Ala  Ser  Ile  Ser  Cys  Arg  Ser  Gln  Ser  Leu  Val  Asn  Ser
               20                       25                      30

Asn  Gly  Asn  Thr  Tyr  Leu  His  Trp  Tyr  Leu  Gln  Lys  Pro  Gly  Gln  Ser
               35                       40                      45

Pro  Lys  Leu  Leu  Ile  Tyr  Lys  Val  Ser  Asn  Arg  Phe  Ser  Gly  Val  Pro
     50                       55                      60

Asp  Arg  Phe  Ser  Gly  Ser  Gly  Ser  Gly  Thr  Asp  Phe  Thr  Leu  Lys  Ile
 65                      70                       75                      80

Ser  Arg  Val  Glu  Ala  Glu  Asp  Leu  Gly  Val  Tyr  Phe  Cys  Ser  Gln  Ser
                    85                       90                      95

Thr  His  Val  Pro  Trp  Thr  Phe  Gly  Gly  Gly  Thr  Lys  Leu  Glu  Ile  Lys
               100                      105                      110
```

( 2 ) INFORMATION FOR SEQ ID NO:5:

( i ) SEQUENCE CHARACTERISTICS:
        ( A ) LENGTH: 339 base pairs
        ( B ) TYPE: nucleic acid
        ( C ) STRANDEDNESS: single
        ( D ) TOPOLOGY: linear ( i i ) MOLECULE TYPE: Protein ( i x ) FEATURE:
        ( A ) NAME/KEY: CDS
        ( B ) LOCATION: 1..339

( x i ) SEQUENCE DESCRIPTION: SEQ ID NO:5:

```
CAG  GTG  CAA  CTC  GTG  GAG  TCT  GGA  CCT  GGC  CTG  GTG  AAA  CCC  TCA  CAG      48
Gln  Val  Gln  Leu  Val  Glu  Ser  Gly  Pro  Gly  Leu  Val  Lys  Pro  Ser  Gln
          115                      120                      125

AGC  CTG  TCC  ATC  ACA  TGC  ACT  GTC  TCT  GGG  TTC  TCA  TTA  TCC  AGA  TAT      96
Ser  Leu  Ser  Ile  Thr  Cys  Thr  Val  Ser  Gly  Phe  Ser  Leu  Ser  Arg  Tyr
          130                      135                      140

AGT  GTA  TAC  TGG  GTT  CGC  CAG  CCT  CCA  GGA  AAG  GGT  CTG  GAG  TGG  CTG     144
Ser  Val  Tyr  Trp  Val  Arg  Gln  Pro  Pro  Gly  Lys  Gly  Leu  Glu  Trp  Leu
145                      150                      155                      160
```

| | | | | | | | | | | | | | | | | |
|---|---|---|---|---|---|---|---|---|---|---|---|---|---|---|---|---|
| GGA | ATG | ATG | TGG | GGT | GGT | GGA | TCC | ACA | GAC | TAT | AAT | TCA | GCT | CTC | AAA | 192 |
| Gly | Met | Met | Trp | Gly | Gly | Gly | Ser | Thr | Asp | Tyr | Asn | Ser | Ala | Leu | Lys | |
| | | | 165 | | | | | 170 | | | | | 175 | | | |
| TCC | AGA | CTG | ACC | ATC | AGC | AAG | GAC | ACC | TCG | AAG | AAC | CAG | GTC | TTC | TTA | 240 |
| Ser | Arg | Leu | Thr | Ile | Ser | Lys | Asp | Thr | Ser | Lys | Asn | Gln | Val | Phe | Leu | |
| | | | 180 | | | | | 185 | | | | | 190 | | | |
| AAA | ATG | AAC | AGT | CTG | CGA | GCT | GAG | GAC | ACA | GCC | ATG | TAC | TAC | TGT | GTC | 288 |
| Lys | Met | Asn | Ser | Leu | Arg | Ala | Glu | Asp | Thr | Ala | Met | Tyr | Tyr | Cys | Val | |
| | | 195 | | | | | 200 | | | | | 205 | | | | |
| AGA | ACC | GAT | GGG | GAC | TAC | TGG | GGT | CAA | GGA | ACC | ACC | GTC | ACC | GTC | TCC | 336 |
| Arg | Thr | Asp | Gly | Asp | Tyr | Trp | Gly | Gln | Gly | Thr | Thr | Val | Thr | Val | Ser | |
| | 210 | | | | | 215 | | | | | 220 | | | | | |
| TCA | | | | | | | | | | | | | | | | 339 |
| Ser | | | | | | | | | | | | | | | | |
| 225 | | | | | | | | | | | | | | | | |

( 2 ) INFORMATION FOR SEQ ID NO:6:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Gln | Val | Gln | Leu | Val | Glu | Ser | Gly | Pro | Gly | Leu | Val | Lys | Pro | Ser | Gln |
| 1 | | | | 5 | | | | | 10 | | | | | 15 |
| Ser | Leu | Ser | Ile | Thr | Cys | Thr | Val | Ser | Gly | Phe | Ser | Leu | Ser | Arg | Tyr |
| | | | 20 | | | | | 25 | | | | | 30 | | |
| Ser | Val | Tyr | Trp | Val | Arg | Gln | Pro | Pro | Gly | Lys | Gly | Leu | Glu | Trp | Leu |
| | | 35 | | | | | 40 | | | | | 45 | | | |
| Gly | Met | Met | Trp | Gly | Gly | Gly | Ser | Thr | Asp | Tyr | Asn | Ser | Ala | Leu | Lys |
| | 50 | | | | | 55 | | | | | 60 | | | | |
| Ser | Arg | Leu | Thr | Ile | Ser | Lys | Asp | Thr | Ser | Lys | Asn | Gln | Val | Phe | Leu |
| 65 | | | | | 70 | | | | | 75 | | | | | 80 |
| Lys | Met | Asn | Ser | Leu | Arg | Ala | Glu | Asp | Thr | Ala | Met | Tyr | Tyr | Cys | Val |
| | | | | 85 | | | | | 90 | | | | | 95 | |
| Arg | Thr | Asp | Gly | Asp | Tyr | Trp | Gly | Gln | Gly | Thr | Thr | Val | Thr | Val | Ser |
| | | | 100 | | | | | 105 | | | | | 110 | | |
| Ser | | | | | | | | | | | | | | | |

( 2 ) INFORMATION FOR SEQ ID NO:7:

( i ) SEQUENCE CHARACTERISTICS:
        ( A ) LENGTH: 336 base pairs
        ( B ) TYPE: nucleic acid
        ( C ) STRANDEDNESS: single
        ( D ) TOPOLOGY: linear ( i i ) MOLECULE TYPE: Protein ( i x ) FEATURE:
        ( A ) NAME/KEY: CDS
        ( B ) LOCATION: 1..336

( x i ) SEQUENCE DESCRIPTION: SEQ ID NO:7:

| | | | | | | | | | | | | | | | | |
|---|---|---|---|---|---|---|---|---|---|---|---|---|---|---|---|---|
| GAC | CTC | CAG | CTG | ACC | CAG | TCT | CCA | CTC | TCC | CTG | CCT | GTC | AGT | CTT | GGA | 48 |
| Asp | Leu | Gln | Leu | Thr | Gln | Ser | Pro | Leu | Ser | Leu | Pro | Val | Ser | Leu | Gly | |
| | 115 | | | | | 120 | | | | | 125 | | | | | |
| GAT | CGA | GCC | TCC | ATC | TCT | TGC | AGA | TCT | AGT | CAG | AGC | CTT | GTA | AAC | AGT | 96 |
| Asp | Arg | Ala | Ser | Ile | Ser | Cys | Arg | Ser | Ser | Gln | Ser | Leu | Val | Asn | Ser | |
| 130 | | | | | 135 | | | | | 140 | | | | | 145 | |

| | | | | | | | | | | | | | | | | |
|---|---|---|---|---|---|---|---|---|---|---|---|---|---|---|---|---|
| AAT | GGA | AAC | ACC | TAT | TTA | CAT | TGG | TAC | CTG | CAG | AAG | CCA | GGC | CAG | TCT | 144 |
| Asn | Gly | Asn | Thr | Tyr 150 | Leu | His | Trp | Tyr | Leu 155 | Gln | Lys | Pro | Gly | Gln 160 | Ser | |
| CCA | AAG | CTC | CTG | ATC | TAC | AAA | GTT | TCC | AAC | CGA | TTT | TCT | GGG | GTC | CCA | 192 |
| Pro | Lys | Leu | Leu 165 | Ile | Tyr | Lys | Val | Ser 170 | Asn | Arg | Phe | Ser | Gly 175 | Val | Pro | |
| GAC | AGG | TTC | AGT | GGC | AGT | GGA | TCA | GGG | ACA | GAT | TTC | ACA | CTC | AAG | ATC | 240 |
| Asp | Arg | Phe 180 | Ser | Gly | Ser | Gly | Ser 185 | Gly | Thr | Asp | Phe | Thr 190 | Leu | Lys | Ile | |
| AGC | AGA | GTG | GAG | GCT | GAG | GAT | GTG | GGA | GTT | TAT | TAC | TGC | TCT | CAA | AGT | 288 |
| Ser | Arg 195 | Val | Glu | Ala | Glu | Asp 200 | Val | Gly | Val | Tyr | Tyr 205 | Cys | Ser | Gln | Ser | |
| ACA | CAT | GTT | CCG | TGG | ACG | TTC | GGT | GGA | GGC | ACC | AAG | CTG | GAA | ATC | AAA | 336 |
| Thr 210 | His | Val | Pro | Trp | Thr 215 | Phe | Gly | Gly | Gly | Thr 220 | Lys | Leu | Glu | Ile | Lys 225 | |

( 2 ) INFORMATION FOR SEQ ID NO:8:

( i ) SEQUENCE CHARACTERISTICS:
        ( A ) LENGTH: 112 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Asp 1 | Leu | Gln | Leu | Thr 5 | Gln | Ser | Pro | Leu | Ser 10 | Leu | Pro | Val | Ser | Leu 15 | Gly |
| Asp | Arg | Ala | Ser 20 | Ile | Ser | Cys | Arg | Ser 25 | Ser | Gln | Ser | Leu | Val 30 | Asn | Ser |
| Asn | Gly | Asn 35 | Thr | Tyr | Leu | His | Trp 40 | Tyr | Leu | Gln | Lys | Pro 45 | Gly | Gln | Ser |
| Pro | Lys 50 | Leu | Leu | Ile | Tyr | Lys 55 | Val | Ser | Asn | Arg | Phe 60 | Ser | Gly | Val | Pro |
| Asp 65 | Arg | Phe | Ser | Gly | Thr 70 | Gly | Ser | Gly | Thr | Asp 75 | Phe | Thr | Leu | Lys | Ile 80 |
| Ser | Arg | Val | Glu | Ala 85 | Glu | Asp | Val | Gly | Val 90 | Tyr | Tyr | Cys | Ser | Gln 95 | Ser |
| Thr | His | Val | Pro 100 | Trp | Thr | Phe | Gly | Gly 105 | Gly | Thr | Lys | Leu | Glu 110 | Ile | Lys |